(12) United States Patent
Khalife et al.

(10) Patent No.: US 12,396,822 B2
(45) Date of Patent: *Aug. 26, 2025

(54) SYSTEMS, METHODS, AND DEVICES FOR TRACKING SURGICAL INSTRUMENTS AND DEVICES

(71) Applicant: SMADE S.A.S., Lyons (FR)

(72) Inventors: Patrick Joseph Khalife, Deerfield, IL (US); Yacouba Sanogo, Chicago, IL (US); David Nicholas Ryan, Rochetaillee sur Saone (FR)

(73) Assignee: SMADE S.A.S., Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/890,527

(22) Filed: Sep. 19, 2024

(65) Prior Publication Data

US 2025/0082434 A1 Mar. 13, 2025

Related U.S. Application Data

(63) Continuation of application No. 17/813,479, filed on Jul. 19, 2022, now Pat. No. 12,121,409.
(Continued)

(51) Int. Cl.
*A61B 90/98* (2016.01)
*A61B 17/00* (2006.01)
*A61B 90/00* (2016.01)

(52) U.S. Cl.
CPC .... *A61B 90/98* (2016.02); *A61B 2017/00221* (2013.01); *A61B 2017/00734* (2013.01); *A61B 2090/0803* (2016.02)

(58) Field of Classification Search
CPC ............................... A61B 90/98; G16H 40/40
See application file for complete search history.

(56) References Cited

U.S. PATENT DOCUMENTS 10,582,985 B2 3/2020 Khalife et al.
12,121,409 B2 * 10/2024 Khalife .................. A61B 90/98
(Continued)

FOREIGN PATENT DOCUMENTS

CA 3081735 11/2020
CN 208641150 3/2019
(Continued)

OTHER PUBLICATIONS

International Search Report and Written Opinion in corresponding International Patent Application No. PCT/US2022/037630, dated Nov. 7, 2022, in 10 pages.

*Primary Examiner* — Matthew Mikels
(74) *Attorney, Agent, or Firm* — Perkins Coie LLP

(57) ABSTRACT

Surgical instrument tracking systems, methods and devices are described. The system can include tracking devices configured to detect location events. The tracking device can include sensors, circuits, power sources, memories, and radio interface. The tracking devices can automatically determine a location of the tracking device when the tracking device detects a location event. The tracking device can automatically transmit the location and information related to the location event to a data analytics platform. The data analytics platform can allow a user to track multiple surgical instruments and surgical instrument tray in order to accurately determine when surgical instruments should be replaced, and how efficiently the surgical instruments are used.

20 Claims, 18 Drawing Sheets

Related U.S. Application Data

(60) Provisional application No. 63/269,661, filed on Mar. 21, 2022, provisional application No. 63/269,565, filed on Mar. 18, 2022, provisional application No. 63/256,085, filed on Oct. 15, 2021, provisional application No. 63/223,909, filed on Jul. 20, 2021.

(56) References Cited

U.S. PATENT DOCUMENTS

| | | |
|---|---|---|
| 2002/0067263 A1 | 6/2002 | Tafoya et al. |
| 2006/0214791 A1 | 9/2006 | Tethrake et al. |
| 2007/0160494 A1 | 7/2007 | Sands |
| 2008/0121703 A1 | 5/2008 | Li et al. |
| 2010/0262139 A1 | 10/2010 | Beller et al. |
| 2013/0274690 A1 | 10/2013 | Greenhalgh et al. |
| 2014/0125482 A1 | 5/2014 | Rigsby |
| 2015/0137972 A1 | 5/2015 | Nepo |
| 2015/0277471 A1 | 10/2015 | Leimbach et al. |
| 2016/0249919 A1 | 9/2016 | Savage et al. |
| 2016/0287265 A1 | 10/2016 | Macdonald et al. |
| 2017/0079641 A1 | 3/2017 | Overmyer et al. |
| 2017/0224400 A1 | 8/2017 | Mistry et al. |
| 2017/0224859 A1 | 8/2017 | Broninx et al. |
| 2017/0296173 A1 | 10/2017 | Shelton, IV et al. |
| 2019/0380792 A1 | 12/2019 | Poltaretskyi |
| 2020/0093485 A1 | 3/2020 | Shelton, IV et al. |
| 2020/0373008 A1 | 11/2020 | Nunes |

FOREIGN PATENT DOCUMENTS

| | | |
|---|---|---|
| CN | 209000388 | 6/2019 |
| EP | 3741248 | 11/2020 |
| GB | 2407187 | 4/2005 |
| KR | 10-2014-0009359 A | 1/2014 |
| KR | 10-2016-0138142 A | 12/2016 |
| WO | WO 2016/075418 | 5/2016 |

* cited by examiner

SYSTEMS, METHODS, AND DEVICES FOR TRACKING SURGICAL INSTRUMENTS AND DEVICES

INCORPORATION BY REFERENCE TO ANY PRIORITY APPLICATIONS

This application is a continuation of U.S. Non-Provisional patent application Ser. No. 17/813,479, filed Jul. 19, 2022, entitled "SYSTEMS, METHODS, AND DEVICES FOR TRACKING SURGICAL INSTRUMENTS AND DEVICES," which claims priority benefit of U.S. Provisional Patent Application No. 63/223,909 filed Jul. 20, 2021, and titled, "SYSTEMS, DEVICES, AND METHODS FOR TRACKING MEDICAL INSTRUMENTS AND/OR DEVICES", U.S. Provisional Patent Application No. 63/256,085 filed Oct. 15, 2021, and titled, "SYSTEMS, DEVICES, AND METHODS FOR TRACKING MEDICAL INSTRUMENTS AND/OR DEVICES", U.S. Provisional Patent Application No. 63/269,565 filed Mar. 18, 2022, and titled, "SYSTEMS, METHODS, AND DEVICES FOR TRACKING SURGICAL INSTRUMENTS AND DEVICES", and U.S. Provisional Patent Application No. 63/269,661 filed Mar. 21, 2022, and titled, "SYSTEMS, METHODS, AND DEVICES FOR TRACKING SURGICAL INSTRUMENTS AND DEVICES", each of which is incorporated herein by reference in its entirety.

Any and all applications for which a foreign or domestic priority claim is identified in the Application Data Sheet as filed with the present application are hereby incorporated by reference under 37 CFR 1.57.

BACKGROUND

Field

The present application relates to surgical devices, instruments, and trays, more specifically surgical devices, instruments, and trays including sensors and devices for geolocation tracking.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

Some embodiments herein relate to a method for tracking surgical instruments and devices, the method comprising: detecting, by a sensor, a location event associated with a surgical instrument; determining, by a communication module, a location of the surgical instrument when the location event is detected; comparing the location of the surgical instrument to a previous location of the surgical instrument stored in a memory to determine that the location of the surgical instrument is different from the previous location of the surgical instrument; and if the location of the surgical instrument is different from the previous location of the surgical instrument, transmitting, by the radio interface the location of the surgical instrument to a data analytics platform.

In some embodiments, the location event can include at least one of an acceleration, a change in temperature, a change in light, or a change in a magnetic field.

In some embodiments, the location event can be an acceleration detected by an accelerometer and/or a vibrometer, and the method can include the steps of: determining a type of acceleration based on at least one of an intensity, or a frequency of the acceleration.

In some embodiments, the method can include the steps of: determining, by a processor, whether the location event reaches a threshold level; and if the location event reaches the threshold level, transmitting, by the radio interface the location to the data analytics platform.

In some embodiments, the method can include the step of determining the location of the surgical instrument after a predetermined time has passed wherein the predetermined time can be between 1 day and 1 month.

In some embodiments, the communication module can be a radio interface.

Some embodiments herein relate to a device for tracking surgical instruments comprising: at least one sensor; configured to detect a location event of the device; a circuit for controlling and processing signals coming from the at least one sensor; a communication module for transmitting information to an external device; a memory for storing information coming from the circuit; and a power source configured to supply power to the at least one sensor, the communication module, the circuit, and the memory, wherein the device is configured to: determine, by the circuit, a location of the surgical instrument tracking device when the at least one sensor detects a location event; compare, by the circuit, the location to a previous location stored on the memory in order to determine that the location is different from the previous location; transmit, by the communication module, the location to a data analytics platform.

In some embodiments, the at least one sensor can include at least one of an accelerometer, a temperature sensor, a photosensor, a pressure sensor, a proximity sensor, or a vibrometer.

In some embodiments, the location event can include at least one of an acceleration, a change in temperature, a change in light, a change in pressure, a change in magnetic field, or a vibration.

In some embodiments, the communication module can be configured to automatically determine the location of the surgical instrument tracking device if the at least one sensor does not detect the location event for a period of time, wherein the period of time can be between 1 day and 1 month.

In some embodiments, the communication module can be a radio interface.

In some embodiments, the at least one sensor can be a temperature sensor, and the location event can be a temperature crossing a temperature threshold from a temperature above the temperature threshold to a temperature below the temperature threshold, and wherein the device is configured to: turn off, by the battery, power to the circuit, the memory, and the communication module, when the temperature sensor detects a temperature above the temperature threshold; turn on, by the battery, power to the circuit, the memory, and the communication module, when the temperature sensor detects the location event;

In some embodiments, the location event can occur when the device is removed from an autoclave, and wherein the device can be configured to: increment, by the circuit, a counter stored in the memory; transmit, by the communication module, the counter to the data analytics platform.

In some embodiments, the surgical instrument tracking device can be coupled to a tray.

Some embodiments herein relate to a surgical instrument tracking system comprising: a tray configured to hold at least one surgical instrument; at least one tracking device coupled to the tray, the tracking device can include: at least one sensor configured to detect a location event of the tray; a circuit for controlling and processing signals coming from the at least one sensor; a communication module for transmitting information to an external device; a memory for storing information coming from the circuit; and a power source configured to supply power to the at least one sensor, the communication module, the circuit, and the memory; a handle configured to fit in the tray, the handle including: at least one sensor configured to detect a location event of the handle; an actuator configured to receive the at least one surgical instrument; a circuit for controlling and processing signals from the at least one sensor and the actuator; a communication module for transmitting information to an external device; a memory for storing information coming from the circuit, the memory including at least one counter; wherein when the at least one sensor of the tracking device detects a location event, the tracking device is configured to: determine, by the circuit, a location of the surgical instrument tracking device when the at least one sensor detects a location event; compare, by the circuit, the location to a previous location stored on the memory in order to determine that the location is different from the previous location; transmit, by the communication module, the location to a secondary device; and wherein when the actuator receives a surgical instrument of the at least one surgical instrument, the handle is configured to: detect, by the actuator, a type of the surgical instrument; increment, by the circuit, a counter associated with the type of the surgical instrument; transmit, by the communication module, a value of each of the at least one counter to the secondary device.

In some embodiments, the secondary device can be a data analytics platform.

In some embodiments, the secondary device can be an RFID tag coupled to the tray, and wherein the RFID tag is configured to transmit the location and the value of each of the at least one counter to a RFID reader.

In some embodiments, the at least one surgical instrument can include an antenna with a portion of the antenna covered by an attachment such that the surgical instrument is undetectable by the handle, wherein when the instrument is removed from the tray, the attachment uncovers the portion of the antenna such that the antenna is readable by the handle.

In some embodiments, the communication module of the tracking device can be a radio interface, and the communication module of the handle can be a radio interface.

In some embodiments, the handle and the at least one surgical instrument can each include a strain detector configured to detect when a user is holding the handle and/or the at least one surgical instrument, and wherein the handle and a power source of the surgical instrument are only powered when the strain detector detects the user is holding the handle and/or the at least one surgical instrument.

BRIEF DESCRIPTION OF THE DRAWINGS

The drawings are provided to illustrate example embodiments and are not intended to limit the scope of the disclosure. A better understanding of the systems and methods described herein will be appreciated upon reference to the following description in conjunction with the accompanying drawings, wherein.

DETAILED DESCRIPTION

Figure 1:
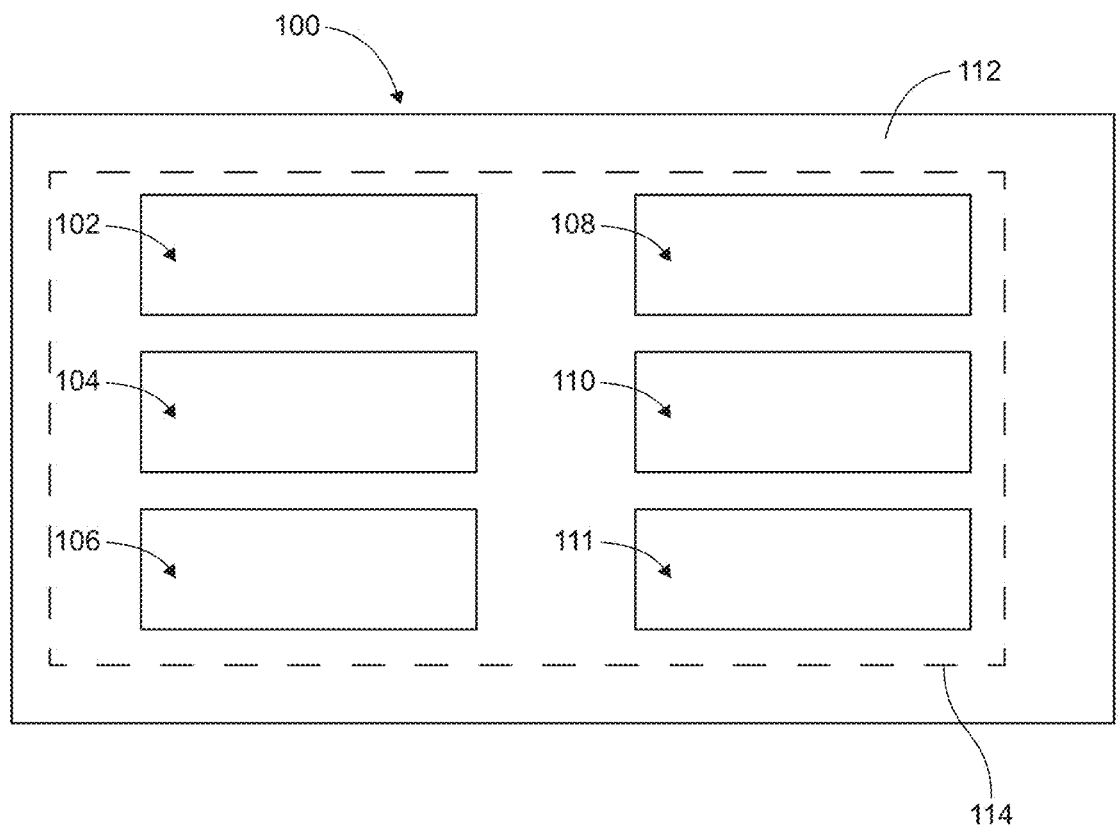
FIG. 1 illustrates a schematic of a tracking device according to some embodiments herein.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present technology.

Tracking the usage of surgical instruments, surgical instrument trays, and other surgical devices can be difficult when the surgical instruments, surgical instrument trays and other surgical devices do not include location trackers. Tracking the number of times a surgical instrument, surgical instrument tray or other surgical device is sterilized in an autoclave must be done manually because electronic components are not configured to withstand high temperatures and pressures of an autoclave. Furthermore, tracking a number of drops or an amount of wear of a surgical instrument surgical instrument tray or other surgical device must be done manually, and doctors or other medical professionals do not actively track how many times surgical instruments surgical instrument trays or other surgical devices are dropped.

For the electronic components to withstand an autoclave, certain electronic components can automatically be powered off when a tracking device is inserted into the autoclave. To track a number of drops or amount of wear of a surgical instrument, surgical instrument tray, or other surgical devices, tracking devices with one or more sensors can be coupled to or embedded within the surgical instruments, the surgical instrument tray, or other surgical devices. In some embodiments, the tracking device can automatically determine a location of the tracking device when the tracking device detects a drop, a change in temperature, a change in light, a change in magnetic field, and/or vibration.

In some embodiments, the systems, devices, and methods may comprise a seamless and lightweight design. In some embodiments, tracking devices can be provided with or without a subscription to a system platform for maintaining and tracking the devices. In some embodiments, a Software-as-a-Service (SaaS) model can be implemented. In some embodiments, the system solution can allow users to choose from a number of subscription formats. In some embodiments, the systems, devices, and methods improve patient safety and reduce the medical device industry footprint in a fast-growing market.

In some embodiments, the systems, devices, and methods provide tailored tracking solutions embedded in medical device that follow regulatory requirements, track device performance, and/or facilitate inventory management through real time device monitoring. In some embodiments, the systems, devices, and methods collect, analyze, and/or process field data through smart devices and/or empower healthcare organizations with insightful information, allowing them to make informed decisions. In some embodiments, the devices can include dual communication capability including at least ultra-high frequency radio-frequency identification (RFID) and low-power wide area network (LPWAN), while staying compliant with electromagnetic compatibility (EMC) standards for medical devices. In some embodiments, the system can transform instruments and trays into self-monitoring smart devices.

Some embodiments herein are directed to systems, methods, and devices for smart medical instrumentation that enables data collection and insightful decision making for safer and more responsible use of medical devices. In some embodiments, provided herein are self-powered medical devices that are resistant to extreme environments, and that collect and deliver invaluable data to the cloud. In some embodiments, the devices described herein are configured to provide data collection from the field. In some embodiments, a data analytics platform is provided to aggregate, normalize, and analyze the data and provide a centralized dynamic user interface for monitoring devices. The embodiments herein may be configured to enable data-powered actions for the field, including optimizing inventory, streamlining processes, and maximizing efficiency of maintenance, replacement, and repair of medical instrumentation.

Devices according to some embodiments herein may be configured to optimize power consumption and power efficiency of a battery embedded within the devices, or otherwise coupled to, the devices. In some embodiments, the devices herein may detect when a module is in motion using one or more sensors within or coupled to the devices. However, in some embodiments, the devices may be held stationary position for relatively long periods of time, such as when the devices are stored. In some embodiments, because continuously monitoring the location of the devices is extremely inefficient for power consumption, and the devices have limited battery power resources, the devices may avoid such continuous monitoring. For example, in some embodiments, one or more sensors of the device may be periodically activated to monitor the location of the devices herein at predetermined times. For example, the one or more sensors may be activated at a time interval of about 1 s, about 5 s, about 10 s, about 20 s, about 30 s, about 1 min, about 5 min, about 10 min, about 30 min, about 1 hour, about 2 hours, about 3 hours, about 4 hours, about 5 hours, about 6 hours, about 7 hours, about 8 hours, about 9 hours, about 10 hours, about 12 hours, about 16 hours, about 1 day, about 2 days, about 3 days, about 4 days, about 5 days, about 6 days, about 7 days, about 8 days, about 9 days, about 10 days, about 20 days, about 30 days, about 1 month, about 2 months, about 3 months, about 6 months, about 1 year, and/or any value between the aforementioned values.

In some embodiments, the devices herein may use an acceleration sensor, or accelerometer, within the devices or coupled to the devices to detect motion of the devices. In some embodiments, the devices may use the acceleration sensor to detect if the devices/instruments are put in motion, either alone, or if a storage platform, such as a hospital/surgical tray, on which the devices/instruments are located is put in motion. In some embodiments, the device may detect wired and/or wireless communication, using hardware and/or software, such as, for example, wireless sniffing, wireless stumbling, or Wi-Fi sniffing, to analyze network communications or packets to obtain network information of networks in proximity to the devices. In some embodiments, the devices may detect network or device information, such as, for example, MAC addresses of a Wi-Fi hotspot or other network node to provide information about the location of the device without using resource intensive sensors such as acceleration sensors. In some embodiments, the devices may obtain accurate geolocation data using network information. In some embodiments, the devices may use a communication protocol or channel, such as a cellular communication channel or Sigfox, to send data wirelessly to the data analytics platform.

In some embodiments, utilizing the devices' wireless communication capabilities may require significant power. In some embodiments, the device may therefore limit wireless communications if the device has not detected movement using periodic monitoring, acceleration sensors, Wi-Fi sniffing, or otherwise. In some embodiments, the devices or the data analytics platform may compare network or device data, such as an obtained MAC address, collected at a first time, to network or device data obtained at a second time. If, for example, the network or device data obtained at the first time is identical to the network or device data obtained at the second time, the device may be configured to limit or eliminate the utilization of any communication hardware and/or software of the devices. In some embodiments, network sniffing or stumbling, such as Wi-Fi sniffing, may be enabled separately from other communication hardware and/or software of the devices.

In some embodiments, the devices herein may use one or more hardware and/or software configurations to obtain network or device data, such as Wi-Fi network information or MAC addresses. In some embodiments, the devices may store the network or device data in one or more computer-readable storage devices. In some embodiments, collection of the network or device data may occur periodically or continuously. In some embodiments, the device may receive network or device data that differs from network or device data that was received at a previous time. In some embodiments, upon receiving contrasting network or device data, the devices may activate communication hardware and/or software of the devices to, for example, connect to a cellular network. In some embodiments, the devices may send data to the data analytics platform, which may comprise a cloud platform, such that the data may be analyzed to provide, for example, a geolocation of the devices.

In some embodiments, the devices may store the network or device data obtained at a first time on an internal memory of the device. In some embodiments, if the devices need to perform geolocation, the device may obtain network or device data at a second time and compare the network or device data obtained at a second time to the network or device data stored on the internal memory. In some embodiments, the devices may detect the network or device data using only Wi-Fi sniffing, without any other communication hardware and/or software. In some embodiments, if the network or device data obtained at a second time is identical or similar to the network or device data stored on the internal memory, the devices may limit or deactivate any other communication hardware and/or software of the device. In this way, the devices described herein may be more power efficient than previously used devices by limiting or eliminating wireless communication capabilities of the device when it is determined that such capabilities are not needed. In some embodiments, the device may comprise one or more communication hardware devices and/or software applications, each of which are configured to be limited or deactivated by the devices according to the methods described above.

In some embodiments, the devices herein may comprise an internal memory that the devices may use to detect and record terminal cycling. In some embodiments, the devices may access the memory in an embedded microcontroller to conduct the comparison of network or device data to determine if a wireless communication phase should be activated. In some embodiments, if the devices do not enter the cellular communication phase, the devices may save energy.

In some embodiments, the devices may utilize an acceleration sensor and Wi-Fi sniffing in combination. For example, if the device requires geolocation, the device may determine internally, or using the data analytics platform, whether the acceleration sensor detected movement since the last recorded communication with the network. In some embodiments, if the acceleration sensor has not detected movement, the device may be configured to avoid Wi-Fi sniffing in order to maximize power efficiency. Thus, in some embodiments, the device may avoid activating any Wi-Fi sniffing capabilities unless movement is detected by an acceleration sensor or another mechanism of the device. In some embodiments, if the accelerometer detects that the device has not undergone any movement, the device may determine that the device has not undergone any movement since a previous geolocation event and avoid wasting valuable resources to verify that the device has not been moved.

In some embodiments, the device may be adapted to provide geolocation services when the device is located on or coupled to a surgical tray. In some embodiments, a surgical tray used to house and move the devices may undergo frequent, but intermittent movement. For example, the surgical tray may be stationary for varied time periods that can range from seconds, minutes, hours, days, or even weeks or months. During this stationary period, the devices described herein may determine that tracking the surgical tray and the device is an unnecessary draw on resources. As such, in some embodiments, the device may adapt, via, for example, user settings, artificial intelligence, or machine learning software, to avoid location tracking during stationary periods. In this way, the geolocation functions of the device may be adapted by a user. In some embodiments, the device may adapt by periodically activating a geolocation function at a predetermined or software-optimized frequency. In some embodiments, the frequency may be based on the, for example, prior determined movements of a surgical tray or based on a machine learning dataset.

In some embodiments, the devices may trigger geolocation in response to one or more high-temperature events, such as autoclaving or other sterilization events. In some embodiments, the devices may use high-temperature events to trigger geolocation functions alone or in combination with the movement monitoring functions described above. For example, in some instances, when a device arrives at a first location, the device may be sterilized. The sterilization may comprise a first high-temperature event. In some embodiments, when the device is moved from the first location to a second location, the device may undergo a second high-temperature event. In some embodiments, if the device triggers geolocation functionality in response to high-temperature events, the device may identify one or more movements of the device without monitoring movement via sensors or other targeted movement monitoring functions.

In some embodiments, the device may comprise a pressure sensor, which may be used to trigger geolocation functionality. For example, the device may identify changes in pressure to determine a level/floor of a building on which the device or a surgical tray holding the device is located.

In some embodiments, the device may comprise a photo sensor. In some embodiments, the photo sensor may be photoelectric. In some embodiments, the photo sensor may detect, for example, if a lid or other covering of a device housing has been opened, such that the device is exposed to light. In some embodiments, activation of the photo sensor may trigger geolocation functionalities. For example, if a lid or other covering of the device housing is opened by a user, the photo sensor may detect light, and the device may be removed from the housing. As such, in some embodiments, detecting an increase or decrease in light by the photo sensor may trigger geolocation to determine if the device was moved from the housing.

In some embodiments, the device may comprise a proximity sensor. In some embodiments, the proximity sensor may comprise an electromagnetic proximity sensor. In some embodiments, a structure proximate to the device, such as the lid or other covering of the device housing, may generate a magnetic field. In some embodiments, if the structure is moved, the strength or direction of the magnetic field may change, and the device proximity sensor may detect that the lid or other covering is open. In other embodiments, the proximity sensor may be a mechanical switch, which may detect any movement of the structure proximate the device. In some embodiments, if the structure generates a magnetic field, the sensor may comprise no moving parts. In some embodiments, the sensor may be sealed in a housing of the device. In some embodiments, activation of the proximity sensor may trigger geolocation functionalities of the device, as activation may indicate that the device was moved.

In some embodiments, the devices described herein may detect vibration using an accelerometer or a vibrometer. In some embodiments, the devices may detect vibration having an intensity above a threshold level. For example, in some embodiments, if the accelerometer or vibrometer detects a vibration below the threshold level, the vibration may be treated as noise and therefore be ignored by the devices. In some embodiments, if the accelerometer or vibrometer detects a vibration above the threshold level, the devices may trigger geolocation functionality. In some embodiments, the device may be configured to determine a type of vibration based on the intensity, frequency, or other properties of the vibration. For example, the device may determine that the device is being transported on, for example, a truck, train, airplane, or otherwise. In some embodiments, the device may differentiate vibrations from differing sources and from noise.

In some embodiments, by using vibration patterns, the device may be able to detect the location of the structure, such as the surgical tray, on which it is located. In some embodiments, detecting the location of a proximate structure, rather than the device itself, may provide a more accurate level of information or more detailed information. For example, in some embodiments, the device may be able to differentiate between various configurations, such as, for example, the device not moving on a shelf, the device being pushed on a trolley or tray, the device being transported on a truck, the device being transported on a train, among others.

In some embodiments, the device may utilize time as a parameter for activating geolocation functions, either alone, or in combination with one or more sensors of the device. For example, even if the device has not felt any vibration, accelerometer indicator, change in temperature, pressure, or magnetic field, if the device has not triggered geolocation for a predetermined period of time, the device may trigger geolocation functionality. In some embodiments, the device may trigger geolocation if the device has not triggered geolocation for about 1 s, about 5 s, about 10 s, about 20 s, about 30 s, about 1 min, about 5 min, about 10 min, about 30 min, about 1 hour, about 2 hours, about 3 hours, about 4 hours, about 5 hours, about 6 hours, about 7 hours, about 8 hours, about 9 hours, about 10 hours, about 12 hours, about 16 hours, about 1 day, about 2 days, about 3 days, about 4 days, about 5 days, about 6 days, about 7 days, about 8 days, about 9 days, about 10 days, about 20 days, about 30 days, about 1 month, about 2 months, about 3 months, about 6 months, about 1 year, and/or any value between the aforementioned values.

In some embodiments, the device may activate geolocation at predetermined time intervals to ensure that the device and all its components are functioning and connected to the network. In some embodiments, if the geolocation malfunctions, the device, a network, or a system may be determined to be defective or dysfunctional and may be flagged for repair or replacement in the data analytics platform, or by one or more alerting mechanisms of the device.

In some embodiments, the device may monitor the usage of one or more smart instruments. In some embodiments, the device may detect when a smart instrument is used. In some embodiments, users may attempt to reduce the number of instruments in, for example, a surgical tray, as the tray may be heavy and expensive to transport or process. In some embodiments, the device may detect if the instrument has been sterilized, if the instrument is located on the tray, and/or if the instrument has been used.

In some embodiments, the devices herein may comprise the instruments or the instruments may have a handle in which the device is located. In some embodiments, the handle may have an accelerometer or other sensor embedded therein. In some embodiments, the device may be able to detect if the smart instrument had been moved. In some embodiments, the handles may be interchangeably connected to one or more shafts comprising various surgical instruments. In some embodiments, the handle may be configured to detect if a shaft has coupled to the handle and if the shaft has been used.

In some embodiments, the handle may comprise a reader and a computer-readable memory. In some embodiments, the handles may be configured to record which smart instrument is used during surgery. In some embodiments, one or more handles may be used, wherein each handle is coupled with the shaft of a surgical instrument. In some embodiment, a device with radio frequency identification (RFID) capabilities may be used as a reader for the device, tray, and/or handle. In some embodiments, the RFID device may download information to the memory and/or communicate the information to the analytics platform.

In some embodiments, the handle may comprise a mechanical sensor, a magnetic sensor, a pressure sensor, or one or more other sensors to determine if handle is coupled with a shaft of an instrument. For example, in some embodiments, the handle may comprise an incidence sensor or electromagnetic sensor. In some embodiments, the handle may comprise a near-field communication (NFC) or RFID near field contact. In some embodiments, a tag may be located on the instrument shaft, such that the tag may be read by the field contact and a reader. In some embodiments, the reader may be located in the handle or in the environment, and the reader may detect if the shaft has been inserted in the handle.

In some embodiments, coupling of the handle to the instrument may trigger a geolocation tracking event or determination event. In some embodiments, coupling of the handle to the instrument may not trigger a geolocation tracking event or determination event.

In some embodiments, the information in the handle may be downloaded to a memory in the device. In some embodiments, the device may download the information to the memory and upload the information to the analytics platform. In some embodiments, the handle may be configured to wirelessly connect to the analytics platform, such as a cloud analytics platform.

In some embodiments, the RFID reader may be attached to the tray. In some embodiments, the reader may be configured to detect an instrument or other device, and its location, in the operating room.

In some embodiments, the handle may be configured to record each instrument, which is coupled to the handle using electromagnetic or NFC tags. In some embodiments, the handle may store the information in a computer-readable memory. In some embodiments, the handle may comprise a modem and/or an antenna to transmit the information to the data analytics platform. In some embodiments, the modem and antenna may be a cellular modem and a cellular antenna.

In some embodiments, the reader may be located on or coupled to a surgical instrument tray. In some embodiments, the handle may transmit information using communications hardware in the handle or the handle may communicate the information through another device on or coupled to the surgical tray, or elsewhere.

In some embodiments, the handle may comprise an impedance sensor. In some embodiments, the impedance sensor may activate one or more hardware devices in the handle upon activation. In some embodiments, the handle may detect by impedance whether a shaft is coupled to the handle. In some embodiments, the handle may comprise an impedance sensor to determine if the handle been used or to limit the power consumption of a hardware device within, or coupled to, the handle. In some embodiments, the impedance sensor may detect if a user is holding the handle or instruments. In some embodiments, the handle or instrument may comprise one or more sensors that must be powered. In some embodiments, it may be desirable to reduce or eliminate power provided to the handle or instrument at certain times to preserve the useful life of the battery. Therefore, in some embodiments, the devices herein may be configured to provide power to the sensors only if the instrument is determined to be in use by a user.

In some embodiments, the impedance sensor may detect whether a user is holding the device or instrument in the user's hands. For example, a strain detector may be powered continuously, or only when a user uses the instruments. As such, the impedance sensor may detect when a user is using the instrument. In some embodiments, the impedance sensor may detect that a user is holding the device. In response, the impedance sensor may activate one or more other sensors. In some embodiments, it may be undesirable to provide power to the one or more other sensors continuously.

In some embodiments, the system may include one or more tags that may be readable in only one state. For example, in some embodiments, the tag may comprise a line, such as an antenna, that may be read when the line is a specific length. In some embodiments, the line may be an RFID tag. In some embodiments, a portion of the line may be hidden and, when uncovered, may change the length of the line such that the tag becomes readable by the reader. In some embodiments, a portion of the line may be hidden such that the tag is unreadable to the reader. In some embodiments, changing the state of the tag may comprise a method for detecting if an instrument is moved. For example, when the instrument is in a surgical tray, the line may be partly hidden by a portion of the tray or device housing. However, when the instrument is removed from the tray or housing, the length of the line may be altered or revealed, such that the tag becomes readable to the reader. In some embodiments, the reader may detect when the instrument has been moved by detecting the tag when it is revealed.

In some embodiments, the instrument may comprise an antenna. In some embodiments, the antenna may comprise a metallic line and an attachment in the tray or device housing may conceal a portion of the line. In some embodiments, the attachment in the tray or device housing may conceal a portion of the antenna and, if the instrument is removed from the tray or device housing, then the line may be revealed and read by the reader. In some embodiments, the line may be readable by the reader when the instrument is located in the tray or the device housing. In some embodiments, a portion of the antenna is hidden when the instrument is located in the tray or device housing, causing the line to have a readable length by the reader. In some embodiments, when the instrument is removed from the tray or the device housing, the RFID may not be readable by the reader. As such, in some embodiments, the device may comprise a passive device as opposed to an active device.

In some embodiments, in order to verify what instruments are used in surgery, if a structure of the tray or device housing is moved, an RFID reader in the tray or device housing may be activated, and the RFID reader may begin scanning the tray or device housing. In some embodiments, the RFID reader may detect the instruments in the tray or device housing.

In some embodiments, the system may scan the tray or device housing periodically to determine what instruments have been removed from the tray or device housing.

In some embodiments, the device can include non-accurate geolocation, or accurate geolocation. A non-accurate geolocation device can detect a city where the device is located. For example, if the device is in Boston, the device can detect that the device is in Boston but may not detect a specific location in Boston. Accurate geolocation can include a geolocation accuracy of within 50 meters or less.

In some embodiments, the device can determine how many times a device is sterilized, a time and/or date when the last sterilization occurred, and/or if the device is dropped during shipment.

In some embodiments, the device can detect an accurate geolocation of the device or a tray the device is attached to. The device can track a location of the device or the tray and determined a path of the device.

In some embodiments, a user can scan the device with an RFID reader. The device can transmit information to the RFID. The information can include a number of devices and/or instruments in the tray, a number of uses of each instrument in the tray, a number of drops of the tray, a number of drops of the devices and/or the instruments, a number of sterilizations of the tray, and/or a number of sterilizations of the devices and/or the instruments. In some embodiments the RFID reader can transmit the information to the cloud or any other computer network via cellular communication.

In some embodiments, the device can be a cold tracker. The cold tracker cannot be subject to high temperatures, or an autoclave. The cold tracker can be attached to a shipment case, a computer, and/or any medical device asset that is not placed in an autoclave.

In some embodiments, the system can include one or more devices, and a user can add or remove devices. In some embodiments, the one or more devices can each have different functionality.

In some embodiments, the device can be placed in and removed from an autoclave. The device can withstand high temperatures and high pressures. The device can detect when the device is in an autoclave by comparing a temperature over time to a temperature profile of an autoclave. The device can detect when the temperature is above a threshold temperature for a period of time. If the temperature is above the threshold or the period of time, the device can shut down or turn off at least a portion of internal components of the device.

In some embodiments, the device can include a housing. The housing can include a heat resistant plastic. In some embodiments, the housing can include a heat resistant weld.

In some embodiments, the housing and shutting down or turning off at least a portion of the internal components of the device can extend or increase a duration of time the device works for, or in other words, a lifetime of the device can be extended.

In some embodiments, a temperature sensor can include one or more high temperature resistors. In some embodiments, the temperature sensor can record a temperature profile of the device at a temperature above the threshold.

Surgical Instrument Tracking

FIG. 1 illustrates a schematic of a tracking device 100. The surgical tracking device can include at least one sensor 102, a circuit 104, a radio interface 106, a memory 108, and a power source 110. The at least one sensor 102 can be configured to detect a location event of a surgical instrument or a surgical instrument tray. The location event can be an acceleration, a change in temperature, a change in light, a change in pressure, a change in magnetic field and/or a vibration. The circuit 104 can be configured to control and/or process signals, data, or other information from the at least one sensor 102 and/or the radio interface 106. The radio interface 106 can be configured to transmit the signals, data, or other information from the at least one sensor 102. In some embodiments, the radio interface 106 can include a cellular antenna and/or an RFID antenna. The memory 108 can be configured to store the signals, data, or other information from at least one sensor 102 and/or the circuit 104. In some embodiments, the tracking device 100 can include a counter 111. The counter can be stored in the memory 108. The circuit 104 can increment the counter 111 when the at least one sensor 102 detects a location event. In some embodiments, the tracking device 100 can include a plurality of counters 111. In some embodiments, as further described below with reference to FIG. 5, the tracking device 100 can be configured to automatically determine a location of the tracking device 100 when the at least one sensor detects a location event, and the tracking device 100 can automatically transmit the location to a computer network on a data analytics platform, as described further below with reference to FIGS. 6-15.

In some embodiments, the power source 110 can use energy harvesting from vibrations and/or thermal cycles to charge. In some embodiments, the tracking device 100 can be coupled to or embedded within a surgical instrument tray, a surgical instrument, and/or an implant.

In some embodiments, the at least one sensor 102 can include an acceleration sensor or an accelerometer. The acceleration sensor can be configured to detect when a surgical instrument or a surgical instrument tray is put in motion. For example, the acceleration sensor can detect when the surgical instrument or surgical instrument tray is picked up, put down, dropped, or otherwise generally moved. In some embodiments, the location event can be the movement of the tracking device 100 detected by the sensor 102. In some embodiments, if the acceleration is greater than a threshold, or a rate of change of the acceleration is greater than a threshold, the tracking device 100, via the sensor 102 and the circuit 104, can determine that the tracking device 100 or the surgical instrument or surgical instrument tray the tracking device 100 is coupled to is damaged. In some embodiments, detection of damage can be a location event.

In some embodiments, the at least one sensor 102 can include a temperature sensor. The temperature sensor can be configured to detect a change in temperature around the device, when the temperature around the device increases above a threshold temperature, and/or when the temperature decreases below a threshold temperature. In some embodiments the temperature sensor can be configured to withstand temperatures above the threshold temperature. The temperatures sensor can include resistors configured to withstand high temperatures. The resistors can include NTC resistors, or resistors with a negative temperature coefficient. In some embodiments, the temperature sensor can be configured to determine when the tracking device 100 is placed in an autoclave and/or removed from an autoclave. In some embodiments, the circuit 104 can be potted with polyurethane comprising thermal dimensional variations. The thermal dimensional variations can prevent internal load that could lead to cracks in the circuit 104. The temperature threshold can be about 250 degrees Fahrenheit to about 375 degrees Fahrenheit. In some embodiments, the temperature threshold can be about 250 degrees Fahrenheit, about 270 degrees Fahrenheit, about 285 degrees Fahrenheit, about 300 degrees Fahrenheit, about 340 degrees Fahrenheit, and/or about 375 degrees Fahrenheit. In some embodiments, the location event can be when the tracking device 100 is placed in and/or removed from the autoclave. In some embodiments the location event can be when the temperature around the device increases above a threshold temperature, and/or when the temperature decreases below a threshold temperature.

In some embodiments, when the at least one sensor 102 detects the temperature around the tracking device 100 increases above the threshold temperature, the circuit 104 can be configured to turn off or cut off power from the power source 110 to the radio interface 106, the memory 108, and/or the counter 111. The circuit 104 can be configured to turn on or supply power from the power source 110 to the radio interface 106, the memory 108, and/or the counter 111 when the sensor 102 detects the temperature around the tracking device 100 decreases below the threshold temperature. In some embodiments, the circuit 104 can automatically increment the counter 111 when the circuit 104 turns on or supply powers.

In some embodiments, the at least one sensor 102 can include a photo sensor. The photo sensor can be configured to detect a change in light. The photo sensor can be configured to detect if a lid or other covering of the tracking device 100 has been opened, such that the tracking device 100 is exposed to light. In some embodiments, the change in light can be a location event.

In some embodiments, the at least one sensor 102 can include a proximity sensor. The lid or other covering of the tracking device 100 can include a device configured to generate a magnetic field. The proximity sensor can be configured to detect a change in the magnetic field when the lid or other covering is opened, closed, or otherwise moved relative to the sensor 102. In some embodiments, the proximity sensor can include a mechanical switch. The mechanical switch can be configured to be activated when the lid or other covering in closed such that when the lid or other covering is open, the switch is deactivated. In some embodiments, the mechanical switch can be configured to be activated when the lid or other covering is open such that when the lid or other covering is closed, the switch is deactivated. In some embodiments, opening and/or closing the lid can be a location event.

In some embodiments, the at least one sensor 102 can include a vibration sensor. The vibration sensor can be an accelerometer or vibrometer. The vibration sensor can be configured to detect a vibration having an intensity above a threshold level. In some embodiments, the vibration can be a location event if vibration sensor detects a vibration having an intensity above the threshold.

In some embodiments, the at least one sensor 102 can include a pressure sensor. The pressure sensor can include a barometer. The pressure sensor can be configured to detect a change in pressure around the tracking device 100. The pressure sensor can detect which floor or level of a building the tracking device 100 is on. For example, the tracking device 100 may be on a first floor of a hospital, and the pressure sensor may detect the change in pressure when the tracking device 100 is taken up to a second floor of the hospital. In some embodiments, the change in pressure can be a location event.

In some embodiments, the at least one sensor 102 can include a sampling rate, and the at least one sensor 102 can increase and/or decrease the sampling rate when the at least one sensor 102 detects a location event.

In some embodiments, by using vibration patterns, the tracking device 100 may be able to detect, via the at least one sensor 102 and the circuit 104, the location of the structure, such as a surgical tray, on which it is located. In some embodiments, detecting the location of a proximate structure, rather than the tracking device 100 itself, may provide a more accurate level of information or more detailed information. For example, in some embodiments, the tracking device 100 may be able to differentiate between various configurations, such as, for example, the tracking device 100 not moving on a shelf, the tracking device 100 being pushed on a trolley or surgical tray, the tracking device 100 being transported on a truck, the tracking device 100 being transported on a train, among others.

In some embodiments, if the tracking device 100 does not detect a location event for a period of time, the tracking device 100 can enter a low power mode. The low power mode can include turning off or cutting off power to one or more internal components 114 of the tracking device 100. In some embodiments, the tracking device 100 can enter the low power mode after about 1 s, about 5 s, about 10 s, about 20 s, about 30 s, about 1 min, about 5 min, about 10 min, about 30 min, about 1 hour, about 2 hours, about 3 hours, about 4 hours, about 5 hours, about 6 hours, about 7 hours, about 8 hours, about 9 hours, about 10 hours, about 12 hours, about 16 hours, about 1 day, about 2 days, about 3 days, about 4 days, about 5 days, about 6 days, about 7 days, about 8 days, about 9 days, about 10 days, about 20 days, about 30 days, about 1 month, about 2 months, about 3 months, about 6 months, about 1 year, and/or any value between the aforementioned values.

Figure 2A:
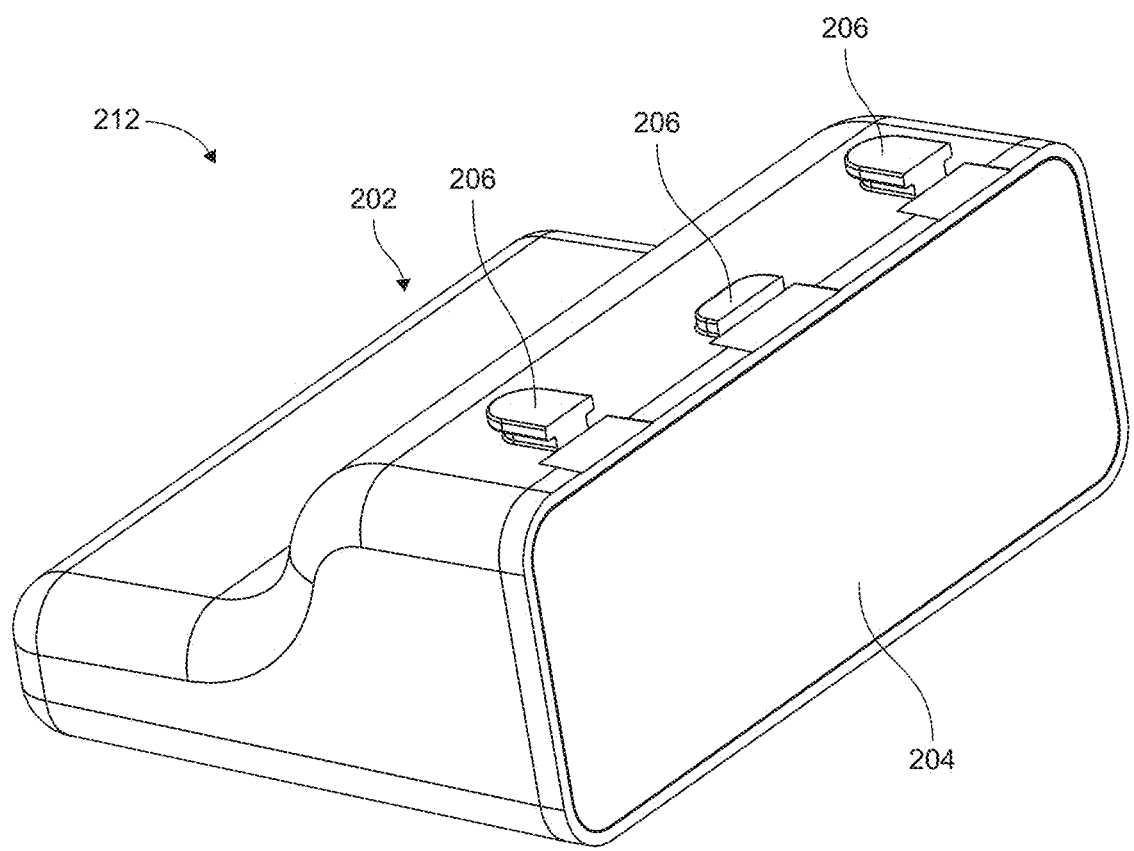
FIGS. 2A-2B illustrate a schematic of a tracking device according to some embodiments herein.
Figure 2B:
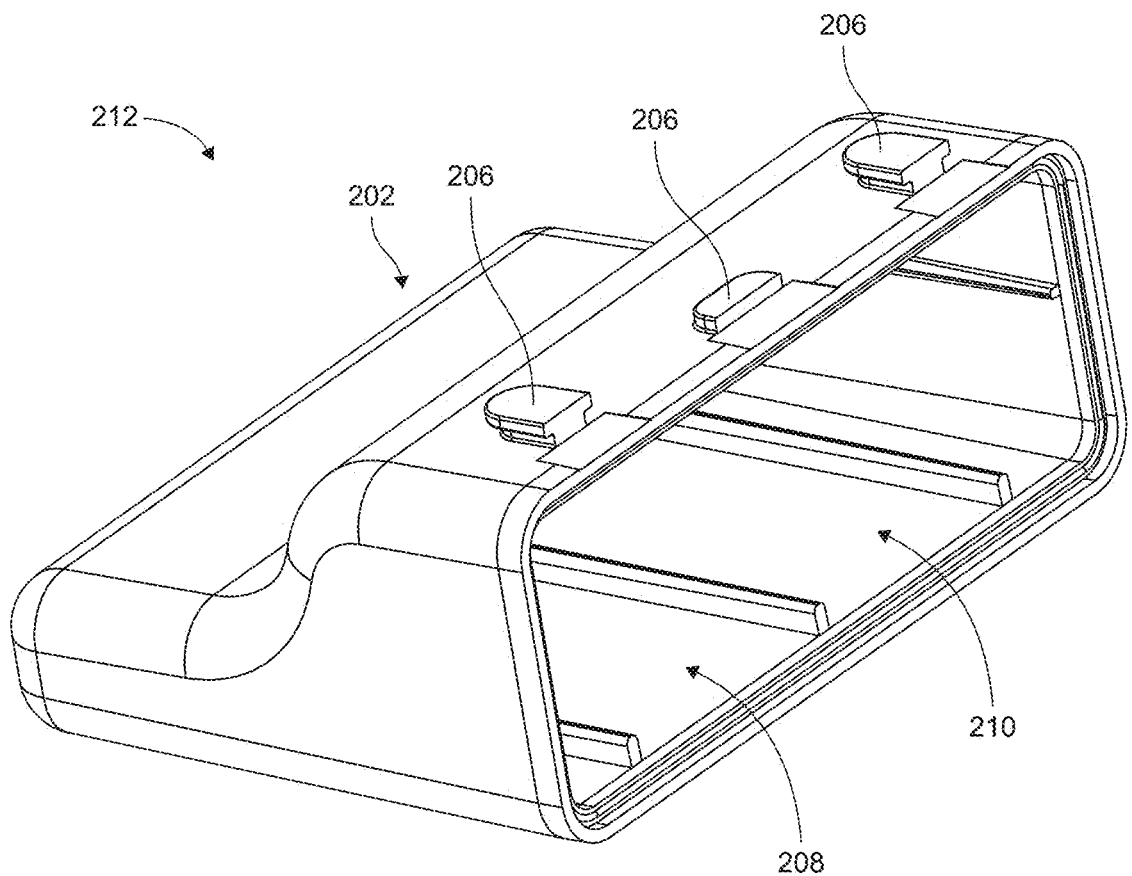

In some embodiments, as shown in FIGS. 1-2B, the tracking device 100 can include a housing 112, 212 configured to house internal components 114. The internal components 114 can include the sensor 102, the circuit 104, the radio interface 106, the memory 108, the power source 110 and the counter 111. The housing 112, 212 can be heat resistant, or heat proof, such that the components are not subject to changes in temperature outside of the housing 112, 212. In some embodiments, the housing 112 include a heat resistant or heat proof plastic, such as RADEL 5500 PPSU. In some embodiments, the housing 112, 212 can be waterproof or water resistant, such that the components are not subject to water or moisture outside the housing 112, 212.

In some embodiments, as shown in FIGS. 2A and 2B, the housing 212 can include a container 202 and a cover 204. The cover 204 can removably attach or couple to an opening 208 in the container 202. When the cover 204 is removed from the container 202, as shown in FIG. 2A, the internal components 114 can be inserted into an interior 210 of the container 202 through the opening 208. The cover 204 can be coupled to the opening 208 and form a heat proof and/or waterproof seal with the container 202. In some embodiments, the cover 204 can be spin welded to the container 202.

In some embodiments, the container 202 can include one or more attachments 206. The attachments 206 can be configured to couple the housing 212 to a tray, as further described below with reference to FIG. 4A.

Figure 3A:
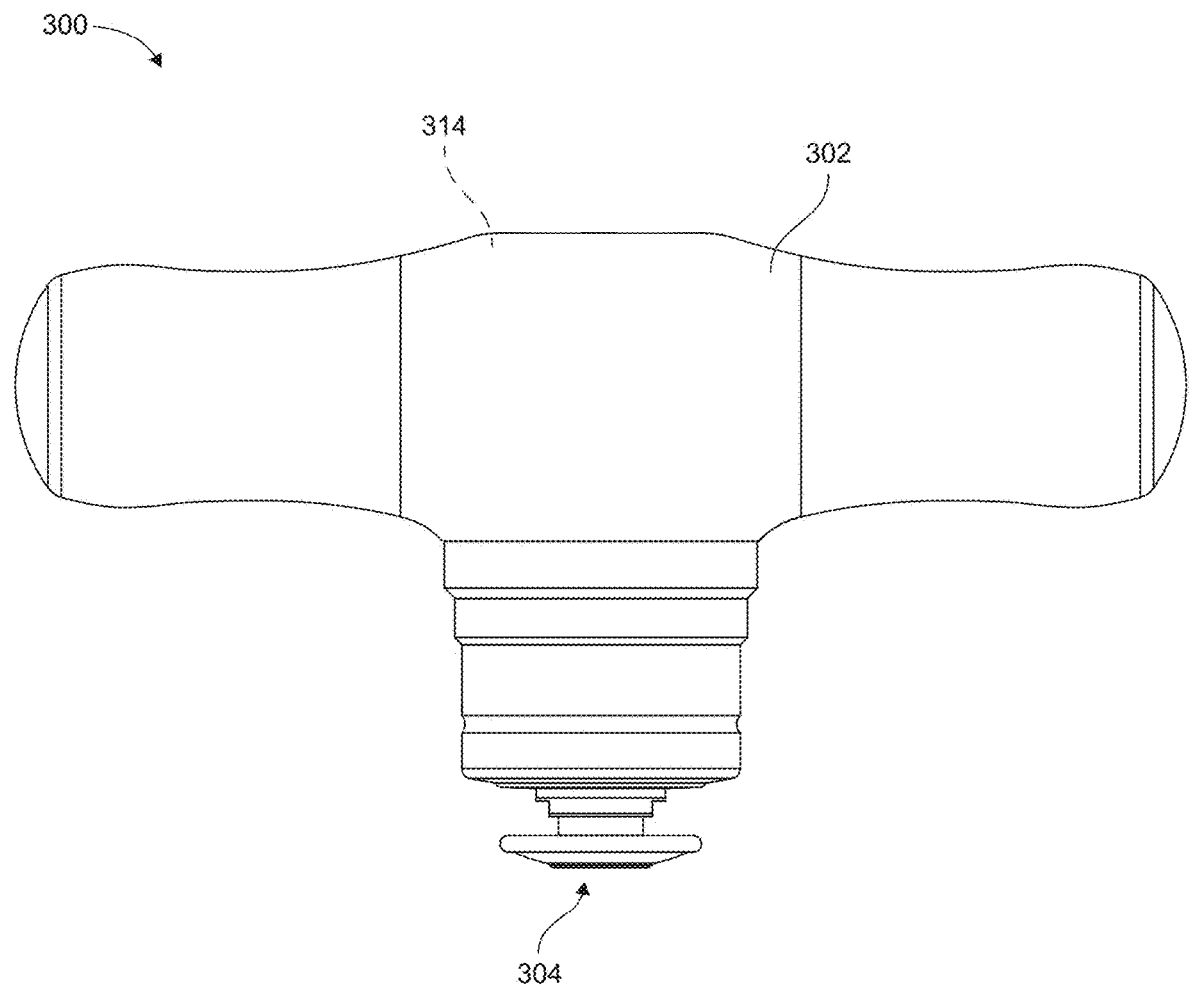
FIGS. 3A-3B illustrate a schematic of a tracking device according to some embodiments herein.
Figure 3B:
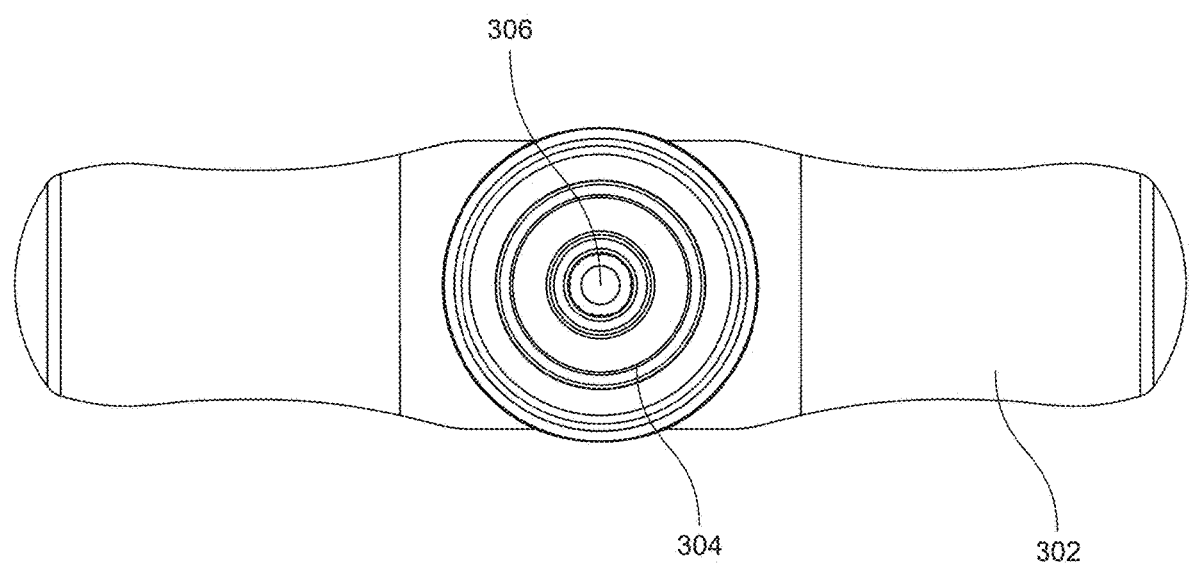

FIGS. 3A and 3B illustrate an alternative tracking device 300. Common features between the tracking device 100 and the tracking device 300 will not be described again but are incorporated here in their entirety. The tracking device 300 can include a handle 302 and an instrument receiver 304. The instrument receiver 304 can be coupled to the handle 302. In some embodiments, the handle 302 can house internal components 314. The instrument receiver 304 can be configured to receive one or more surgical instruments. The instrument can include an actuator 306. The actuator 306 can be configured to increment a counter when the one or more surgical instruments are inserted into the instrument receiver 304. In some embodiments, the actuator 306 can be a torque limiter. The torque limiter can be configured to increment the counter when the one or more surgical instruments actuates the torque limiter. In some embodiments, the tracking device can include a strain detector. The strain detector can determine when a user is using or holding the tracking device 300, and the tracking device 300 can prevent the torque limiter incrementing the counter, unless the strain detector determine the user is using or holding the tracking device 300. In some embodiments, the strain detector can be coupled to or embedded in the one or more surgical instruments. In some embodiments, the tracking device 300 can include metal.

Figure 4A:
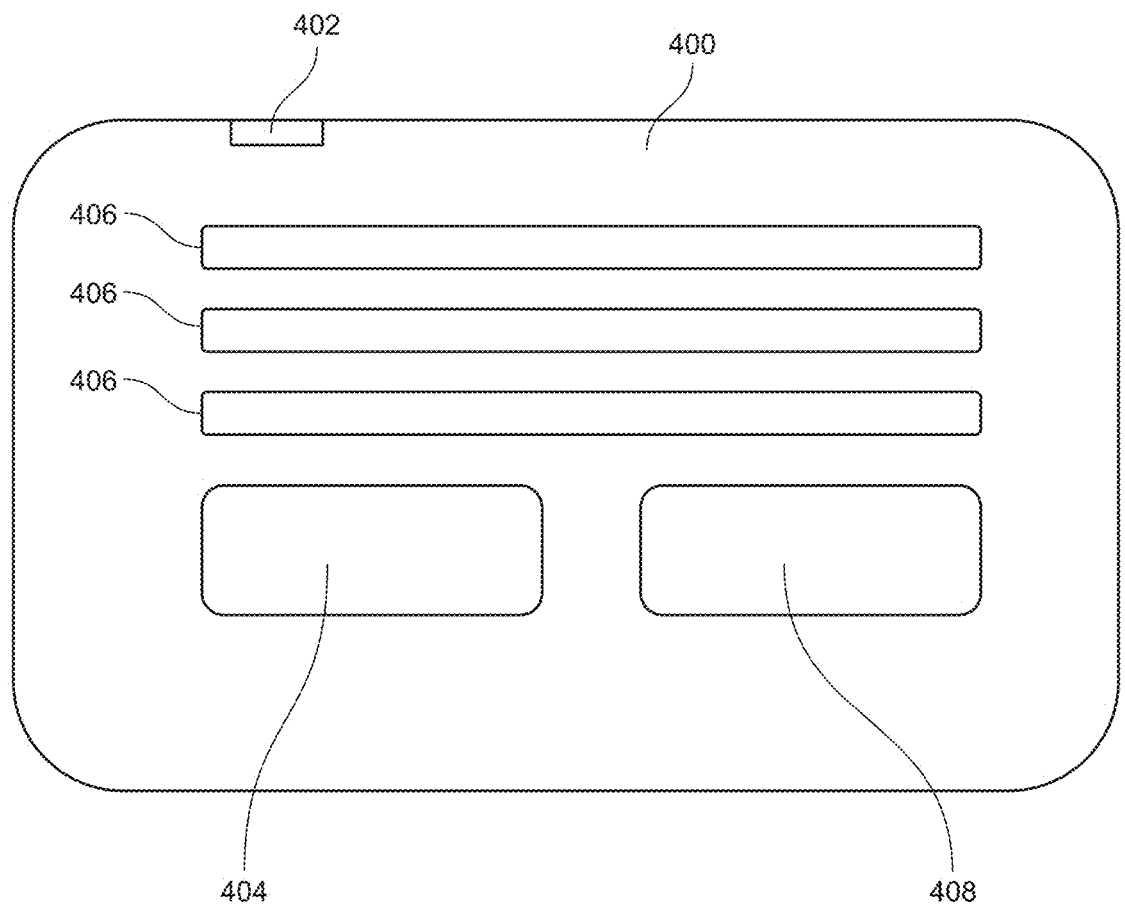
FIG. 4A illustrates a schematic of a surgical tray with a tracking device according to some embodiments herein.
Figure 4B:
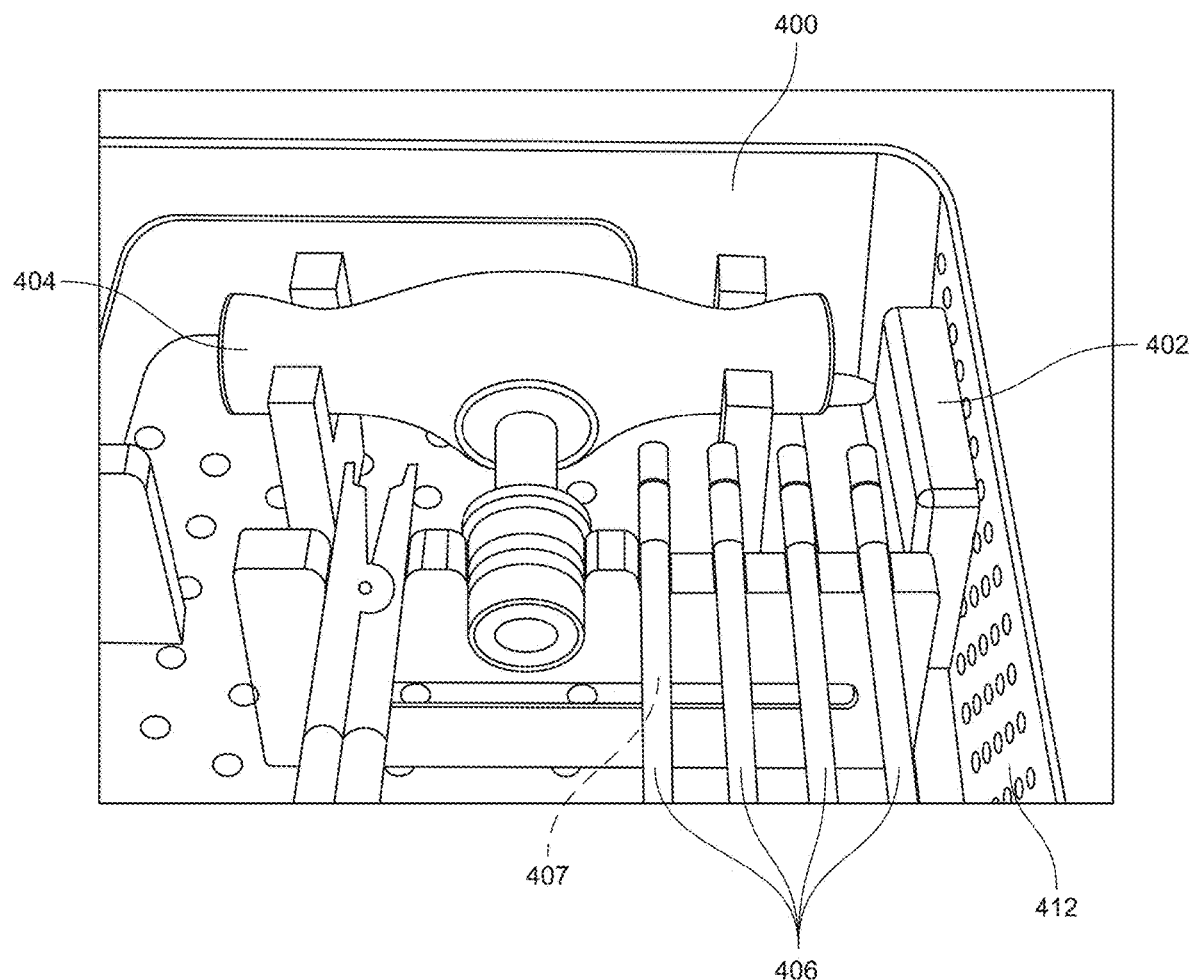
FIG. 4B illustrates a schematic of a surgical tray with a tracking device according to some embodiments herein.

FIGS. 4A and 4B illustrate a tray 400 for transporting one or more surgical instruments 406. The tray 400 can include a first tracking device 402 coupled to the tray 400. In some embodiments the first tracking device 402 can be the tracking device 100 described above. In some embodiments the first tracking device 402 can be the tracking device 100 with housing 212. The housing 212 can be coupled to one or more holes 410 in the tray 400 via the one or more attachments 206 of housing 212. In some embodiments the tray 400 can include a second tracking device 404. The second tracking device 404 can be the tracking device 300 described above. In some embodiments, the tray can include a plurality of first tracking devices 402 wherein each first tracking device 402 is the tracking device 100 with different internal components 114.

The surgical instruments 406 can be smart instruments. The surgical instruments 406 can include internal components 407. The internal components 407 can include the same internal components 114 of tracking device 100 described above. In some embodiments, a location event can include when the surgical instruments 406 are removed from the tray and/or activate the actuator 306 of the tracking device 300. In some embodiments, the surgical instruments 406 can communicate with the first or second tracking devices 402, 404 via RFID. In some embodiments, the first and/or second tracking device 402, 404 can include RFID antenna that can transfer data through metal.

In some embodiments, the internal components 407 can include an antenna. The antenna can include a metallic line. An attachment 412 of the tray can block or cover a portion of the antenna such that the antenna may not communicate with other devices. When the surgical instruments 406 are removed from the tray, the portion of the antenna blocked or covered by the attachment 412 may be revealed and the antenna may communicate with other devices.

In some embodiments, the tray 400 can include a secondary device 408. In some embodiments the secondary device 408 can include an RFID reader. The RFID reader can be configured to communicate with one or more of the first tracking device 402, the second tracking device 404, and the surgical instruments 406. The RFID can retrieve information from a memory of each of the first tracking device 402, the second tracking device 404, and/or the surgical instruments 406. In some embodiments, the information can include a location of each of the first tracking device 402, second tracking device 404 and/or the surgical instruments 406. In some embodiments, the information can include a counter of each of the first tracking device 402, second tracking device 404 and/or the surgical instruments 406. In some embodiments, the secondary device 408 can include a memory configured to store the retrieved information. In some embodiments, the secondary device 408 can be coupled to the tray 400. The secondary device 408 can be coupled to a cover of the tray 400, a sidewall of the tray 400, or any other portion of the tray 400.

In some embodiments, the secondary device 408 can include an accelerometer configured to detect when the tray 400 is moved. In some embodiments, a sensor in the first tracking device 402, the second tracking device 404, and/or the surgical instruments 406 can automatically detect when the tray 400 and/or the surgical instruments 406 are moved. In response to a detected movement of the tray 400 and/or the surgical instruments 406, the secondary device 408 can automatically retrieve information from the first tracking device 402, the second tracking device 404, and the surgical instruments 406.

In some embodiments, the secondary device 408 can periodically retrieve the information from the first tracking device 402, the second tracking device 404, and the surgical instruments 406 to determine what surgical instruments 406 have been removed from the tray 400. The secondary device 408 can periodically retrieve the information after about 1 s, about 5 s, about 10 s, about 20 s, about 30 s, about 1 min, about 5 min, about 10 min, about 30 min, about 1 hour, about 2 hours, about 3 hours, about 4 hours, about 5 hours, about 6 hours, about 7 hours, about 8 hours, about 9 hours, about 10 hours, about 12 hours, about 16 hours, about 1 day, about 2 days, about 3 days, about 4 days, about 5 days, about 6 days, about 7 days, about 8 days, about 9 days, about 10 days, about 20 days, about 30 days, about 1 month, about 2 months, about 3 months, about 6 months, about 1 year, and/or any value between the aforementioned values.

In some embodiments, information of the surgical instruments 406 can be transferred to the second tracking device 404 before the secondary device 408 retrieves information from the second tracking device 404.

In some embodiments, the secondary device 408 can automatically send the retrieved information to an external device. The secondary device 408 can send the retrieved information via a cellular network, W-Fi, Bluetooth, or any other communication network protocols. In some embodiments, the external device can include a computing device and/or a computer network. In some embodiments, the external device can include a data analytics platform, as described below with reference to FIGS. 6-14.

In some embodiments, a user can retrieve the information from the secondary device 408 with a device configured to retrieve information from the secondary device 408. In some embodiments, the device configured to retrieve information can include an RFID reader.

In some embodiments, the first tracking device 402, the second tracking device 404, the surgical instruments 406 can each transmit data to a data analytics platform or a computer network via a cellular antenna or radio interface.

Figure 5:
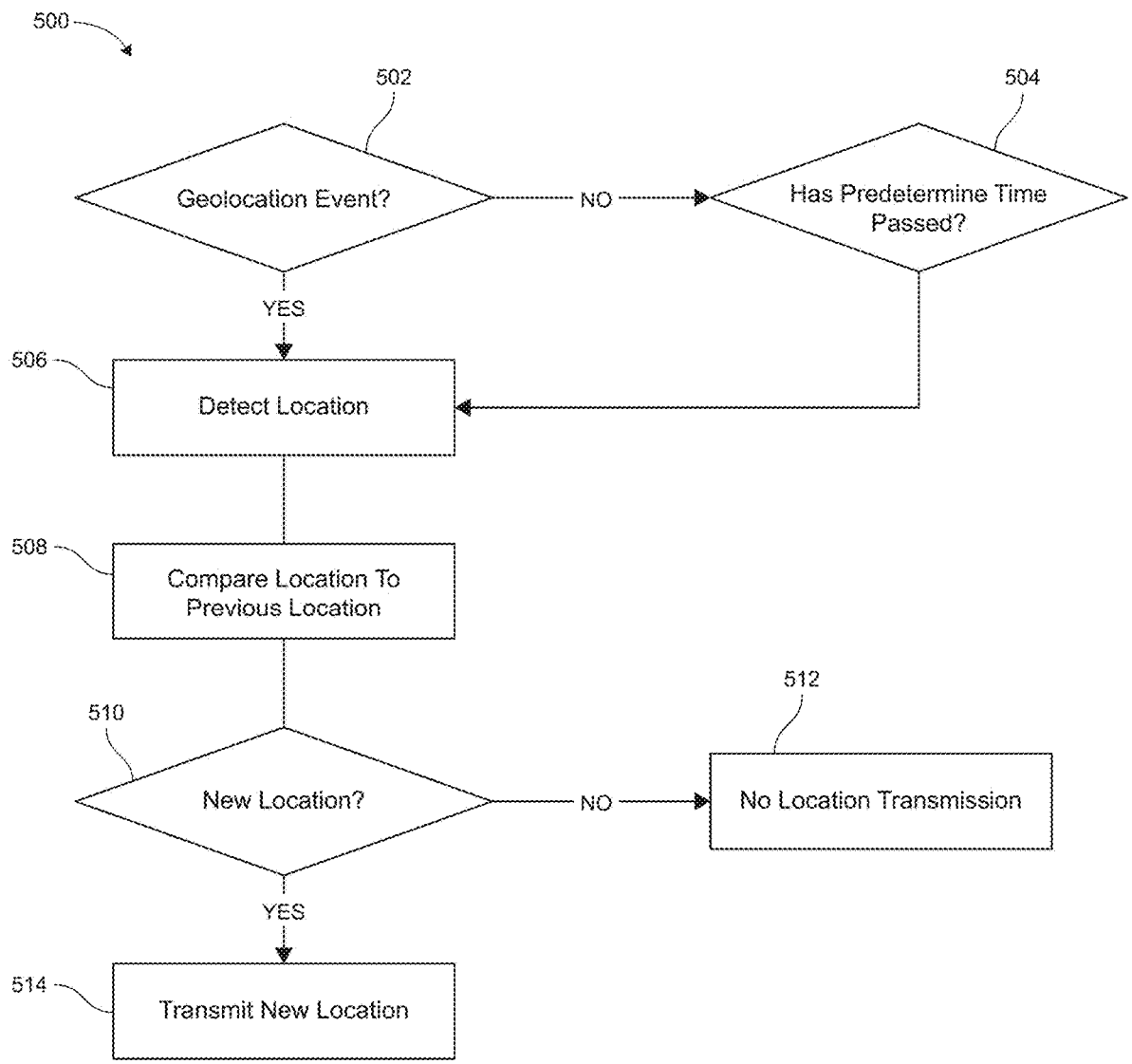
FIG. 5 illustrates a schematic of a method of surgical instrument tracking according to some embodiments herein.

FIG. 5 illustrates a flowchart of a method of determining the location of a tracking device described above with reference to FIGS. 1-4B. In some embodiments, at step 502 the tracking device, a sensor of the tracking device, a circuit of the tracking device or the system can determine if a location or geolocation event has occurred. As described above, the location event or geolocation event can be an acceleration, a change in temperature, the device a change in light, a change in pressure, a change in magnetic field, a vibration, and/or when the tracking device is placed in or removed from an autoclave.

In some embodiments, if the tracking device includes an acceleration sensor, and the location event is an acceleration or a vibration, the tracking device, the circuit or the system can compare a profile of the acceleration and/or vibration to one or more acceleration and/or vibration templates. In some embodiments, the profile can include an intensity and/or a frequency of the acceleration and/or vibration. The tracking device, the circuit, or the system can compare the profile to the template in order to determine a type or category of the acceleration and/or vibration. In some embodiments, certain types or categories of the acceleration and/or vibration can be location events, and other types or categories of the acceleration and/or vibration can not be location events. For example, the template can be an acceleration template of when the tracking device is dropped. The tracking device, the circuit, or the system can automatically categorize a profile as a drop and determine that the drop is a location event. Additionally, the template can be an acceleration or vibration template of when the device is moving on a truck or a cart. The tracking device, the circuit, or the system can automatically categorize a profile as the tracking device moving on a truck or cart and determine that the acceleration and/or the vibration is not a location event.

In some embodiments, if the tracking device detects a location event at step 502, the tracking device can detect a location of the tracking device at step 506. In some embodiments, the radio interface can communicate via Wi-Fi, Bluetooth, near-field communication (NFC), cellular network, and/or any other type of wireless communication. Wireless communication, such as cellular communication can require significant power. In some embodiments, the tracking device can therefore limit wireless communication if the device has not detected a location event. To limit wireless communication, the tracking device can obtain network or device data via network sniffing or stumbling, such as Wi-Fi sniffing. The tracking device can, via the radio interface and/or the circuit, obtain Wi-Fi network information and/or a MAC address of the tracking device when the tracking device detects the location event. The tracking device via the circuit, or a microprocessor stored in a memory of the tracking device, can compare the Wi-Fi network information and/or the MAC address to previously obtained Wi-Fi network information and/or a MAC address stored in the memory of the tracking device.

In some embodiments, if the tracking device does not detect a location event, the tracking device can, at step 504, determine if a predetermined time has passed since a previous location event. If the predetermined time has passed, the tracking Wi-Fi network information and/or the MAC address of the tracking device at step 506. In some embodiments, the device may obtain Wi-Fi network information and/or the MAC address of the tracking device if the device has not obtained Wi-Fi network information and/or the MAC address of the tracking device for about 1 s, about 5 s, about 10 s, about 20 s, about 30 s, about 1 min, about 5 min, about 10 min, about 30 min, about 1 hour, about 2 hours, about 3 hours, about 4 hours, about 5 hours, about 6 hours, about 7 hours, about 8 hours, about 9 hours, about 10 hours, about 12 hours, about 16 hours, about 1 day, about 2 days, about 3 days, about 4 days, about 5 days, about 6 days, about 7 days, about 8 days, about 9 days, about 10 days, about 20 days, about 30 days, about 1 month, about 2 months, about 3 months, about 6 months, about 1 year, and/or any value between the aforementioned values. In some embodiments, the tracking device can obtain Wi-Fi network information and/or the MAC address of the tracking device to ensure that the tracking device and all its components are functioning and connected to the network. If the tracking device malfunctions and is unable to obtain Wi-Fi network information and/or the MAC address, the tracking device, the network, and/or the system can be determined to be defective or dysfunctional and can be flagged or marked for repair or replacement in the data analytics platform, or by one or more components of the device.

In some embodiments, the tracking device can compare the Wi-Fi network information and/or the MAC address of the tracking device to a previously obtained Wi-Fi network information and/or the MAC address of the tracking device at step 508. The tracking device can determine, at step 510, whether the Wi-Fi network information and/or the MAC address are different from the previously obtained Wi-Fi network information and/or the MAC address, the tracking device can save the obtained Wi-Fi network information and/or the MAC address on the memory.

If the Wi-Fi network information and/or the MAC address is different from the previously obtained Wi-Fi network information and/or the MAC address, the tracking device, at step 514, can transmit a location of the tracking device to the system or the data analytics platform via a cellular network. The tracking device can save the obtained Wi-Fi network information and/or the MAC address on the memory. In some embodiments, the location of the tracking device can be based on the obtained Wi-Fi network information and/or the MAC address. In some embodiments, the location can be the location of the tracking device determined via a global navigation satellite system (GNSS) such as global positioning system (GPS). The location of the tracking device can be a longitude and a latitude of the tracking device, a building associated with the location of the tracking device, and/or a general location of the device, such as a city, a county, a state, and/or a country associated with the location of the device.

In some embodiments, if the Wi-Fi network information and/or the MAC address is the same the previously obtained Wi-Fi network information and/or the MAC address, the tracking device, at step 512, can save power and not transmit the location of the tracking device to the system or the data analytics platform.

Data Analytics Platform

In some embodiments, one or more tracking devices and/or smart instruments can be connected to and communicate via the data analytics platform. FIGS. 6-12 illustrate various embodiments and functions of the data analytics platform. The data analytics platform can be a computer system or computer application connected to a computer system. In some embodiments, the computer application can be configured to run on a computing device, a mobile computing device, smart glasses, virtual reality (VR) glasses, a tablet, or any other device.

Figure 6:
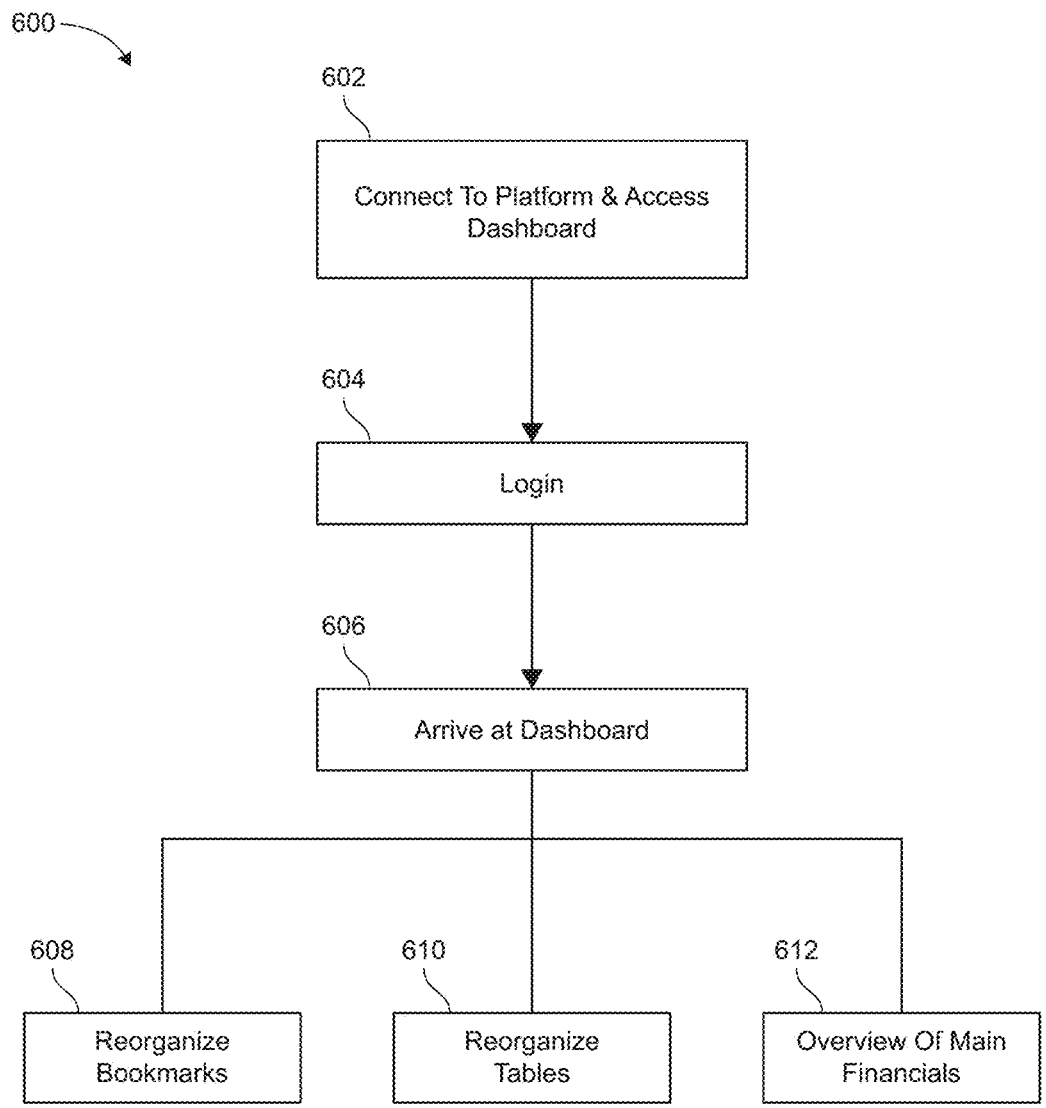
FIG. 6 illustrates a schematic of a method of connecting a user to a central platform according to some embodiments herein.

FIG. 6 illustrates a method 600 of connecting a user to the data analytics platform. At step 602 a user can connect a device to the data analytics platform and access a dashboard. The dashboard can be a graphical user interface (GUI) displayed on the device. In some embodiments, the data analytics platform can require a user to sign into an account at step 604. A user can sign in via an account identification and/or a password. In some embodiments, the account identification can be an email address and/or a username. In some embodiments, the user can login with a biometric input. The biometric input can include a fingerprint, a retinal scan, a face scan, a user's voice, or any other biometric input.

In some embodiments, after the user logs in to the data analytics platform, the system can display a dashboard to the user at step 606 as described below with reference to FIG. 13. In some embodiments, the data analytics platform can allow the user to reorganize one or more bookmarks 608, reorganize one or more tables or data charts displayed to the user 610. The data analytics platform can additionally display an overview of the user's financials 612. The overview of the user's financials can include subscription pricing, costs of tracking devices, a calculated money save from use of the system, and/or any other relevant financial information. In some embodiments, the data analytics platform can be a subscription, a one-time purchase, a software as a service (SaaS), or any other financial structure.

Figure 7:
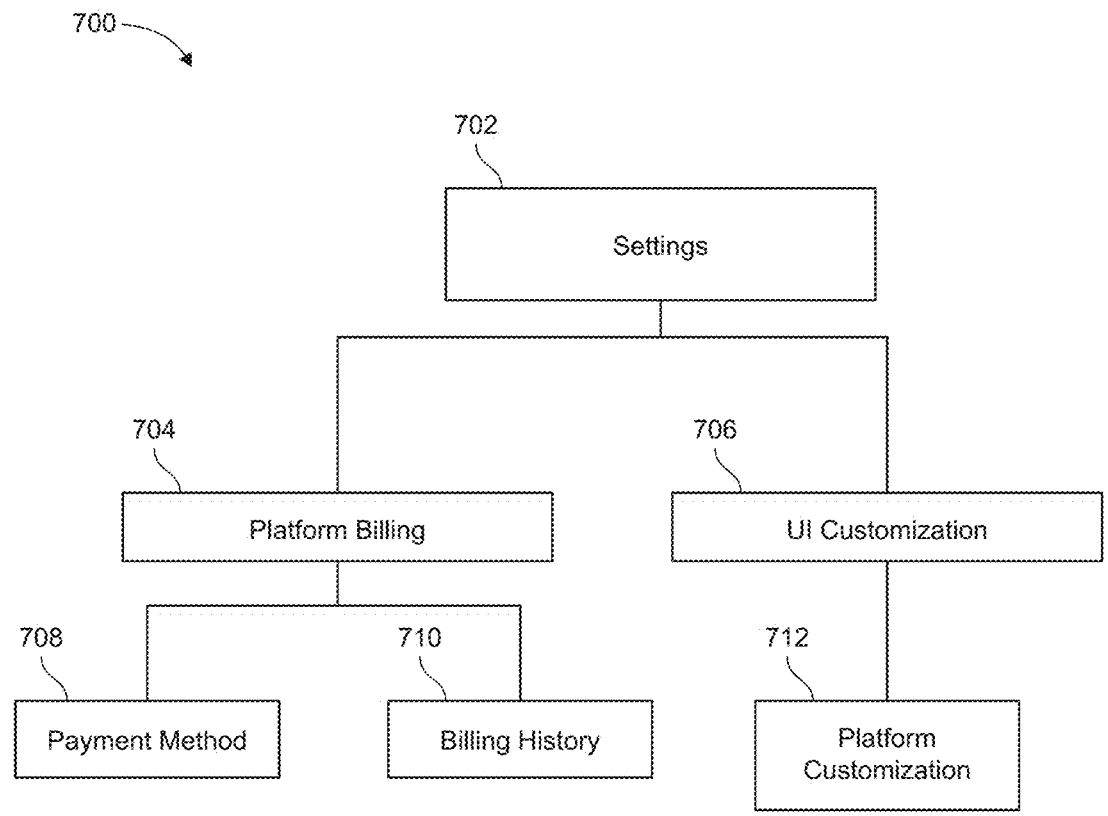
FIG. 7 illustrates a schematic of displaying settings of a central platform to a user according to some embodiments herein.

In some embodiments, as shown in FIG. 7, the data analytics platform can include settings 700 that can be displayed to a user. The data analytics platform can include a settings page 702. In some embodiments, the data analytics platform can display the setting page 702 after the user selects a setting button or selection displayed on the display of the device. The settings page 702 can display platform billing 704 and user interface (UI) customization 706. The platform billing 708 can include a display of the user's payment method. In some embodiments the platform billing can allow a user to update a payment method or supply multiple payments methods for different portions of the data analytics platform. The platform billing 704 can also display a billing history 710. The billing history 710 can include the user's previous bills and/or charges to the user's payment methods. The UI customization 706 can include options for platform customization 712. The platform customization 712 can include options to allow a user to add and/or remove devices from the user's account, add and/or remove one or more additional users to the user's account, select one or more display colors of the data analytics platform, select information calculated and/or displayed by the data analytics platform, and/or any other platform or UI customizations.

Figure 8:
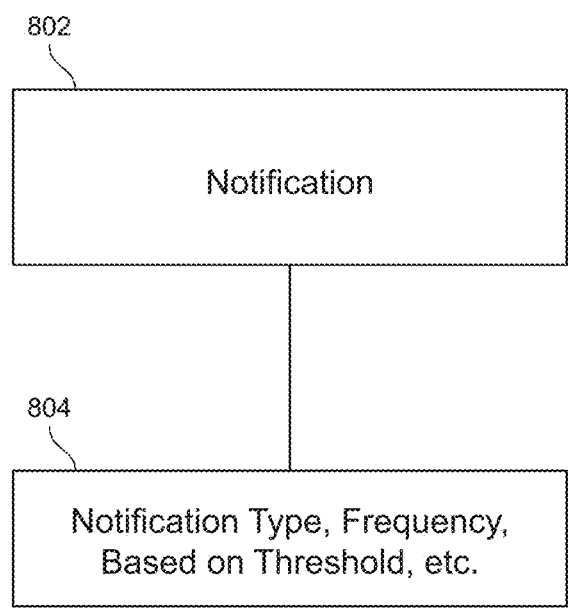
FIG. 8 illustrates a schematic of a method of displaying a notification to a user according to some embodiments herein.

In some embodiments, as shown in FIG. 8, the data analytics platform can send the user one or more notifications 802 and/or display one or more notifications 802 on the device. A format of the one or more notifications 802 can be based one or more factors 804. The one or more factors 804 can include a notification type, a frequency of notifications selected by the user, a threshold, or any other factor. For example, the notification type can be a billing notification. The billing notification can be sent to the user via email and/or displayed in the settings page of the data analytics platform. Additionally, in other examples, the notification type can be a location event notification. The location event notification can be a push notification and/or displayed on a dashboard of the data analytics platform. In some embodiments, the user can select how notifications are sent of displayed based on the one or more factors 804. In some embodiments, the one or more notifications 802 can be displayed on the data analytics platform, and can be sorted by function, type, frequency, order received or sent, or any other notification category.

Figure 9:
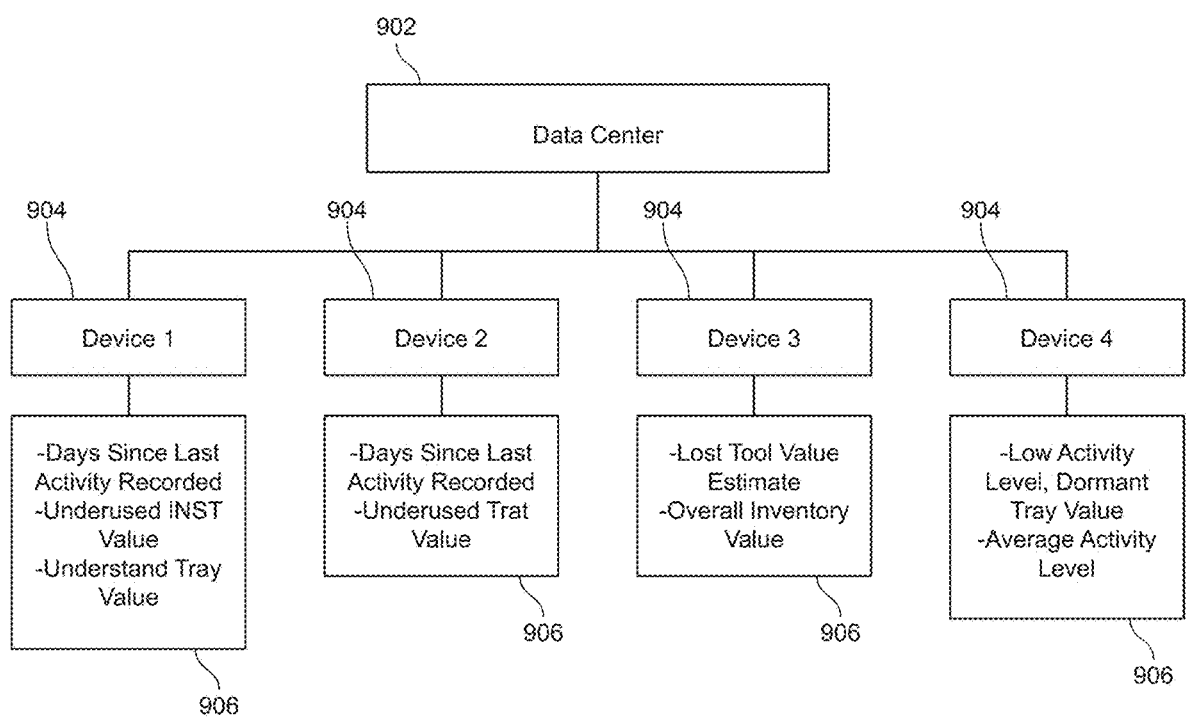
FIG. 9 illustrates a schematic of a data center according to some embodiments herein.

In some embodiments, as shown in FIG. 9, the data analytics platform can include a data center 902. The data center 902 can display or include information 906 about one or more tracking devices 904. The information can include a time since a previous activity or location event, an underused instrument value, an underused tray value, a lost toll value estimate, an overall inventory value, a low activity level, a dormant tray value, an average activity level, and/or any other information 906 associated with the tracking devices. In some embodiments, the data analytics platform can calculate the information 906 based at least in part on location events of each device, and recorded locations of each device.

Figure 10:
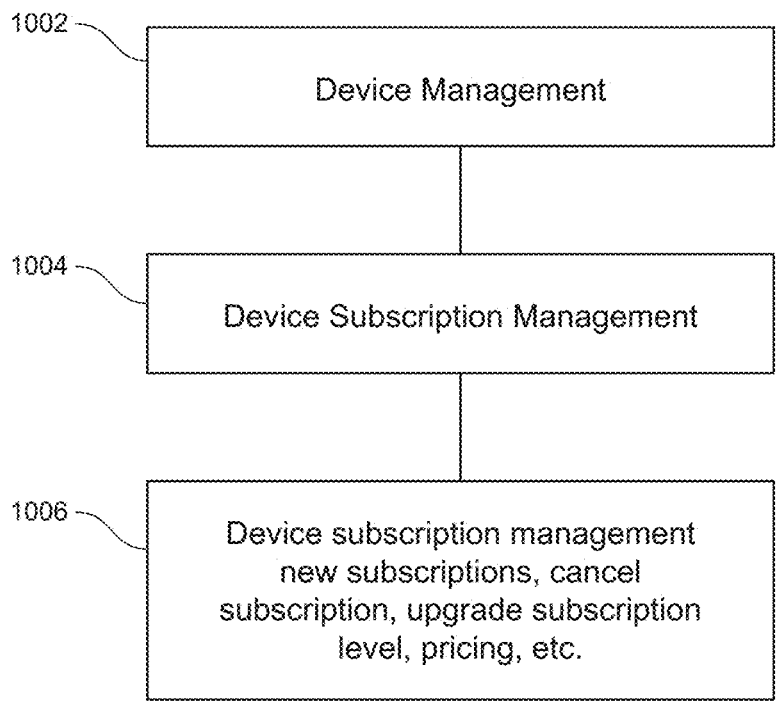
FIG. 10 illustrates a schematic of device management according to some embodiments herein.

In some embodiments, as shown in FIG. 10, the data analytics platform can include a device management page 1002. The device management page 1002 can include device subscription management 1004. The device subscription management 1004 can include one or more options 1006. The options 1006 can include selections to add new subscriptions, cancel subscriptions, upgrade subscription level, and/or any other subscription selections. In some embodiments, the options 1006 can include a display of current subscription levels, pricing for each current subscription level, pricing for all current subscriptions, pricing for upgrading subscription level, and/or any other subscription information and pricing.

Figure 11:
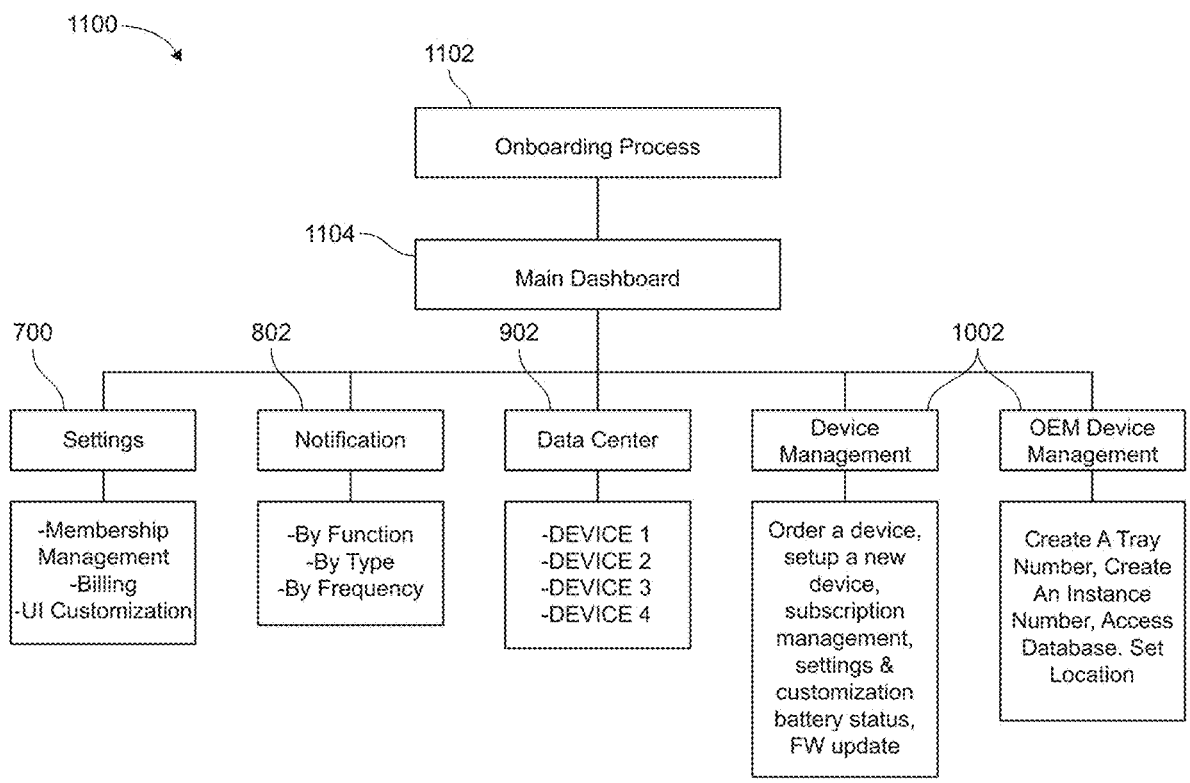
FIG. 11 illustrates a schematic of a central platform according to some embodiments herein.
Figure 12:
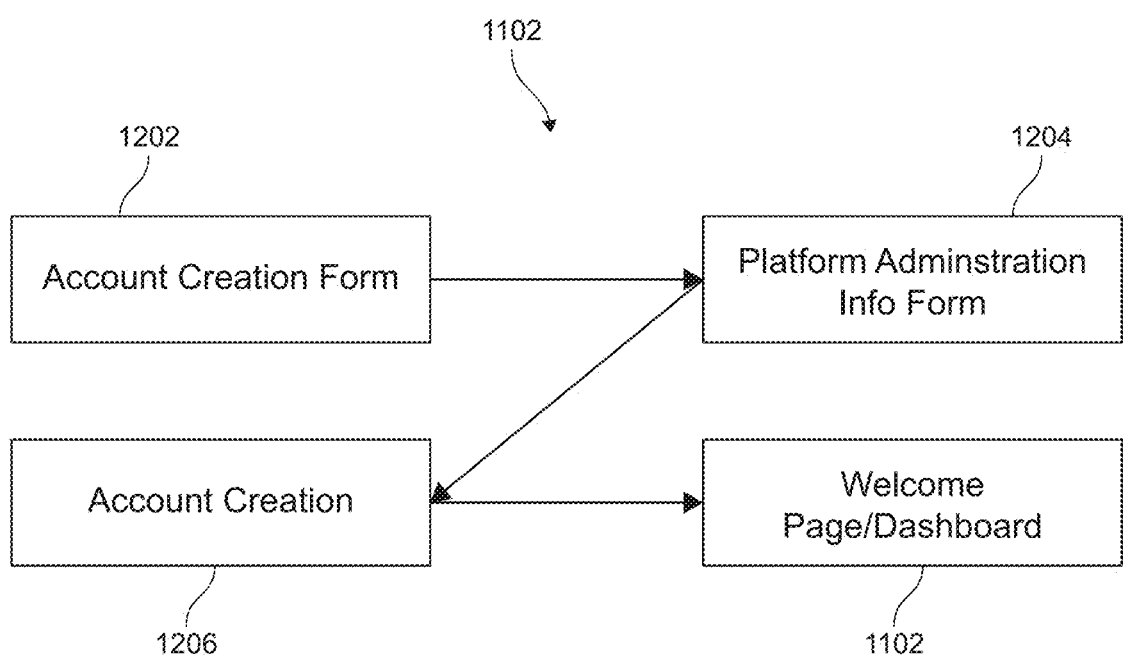
FIG. 12 illustrate a schematic of a method of account creation according to some embodiments herein.
Figure 13:
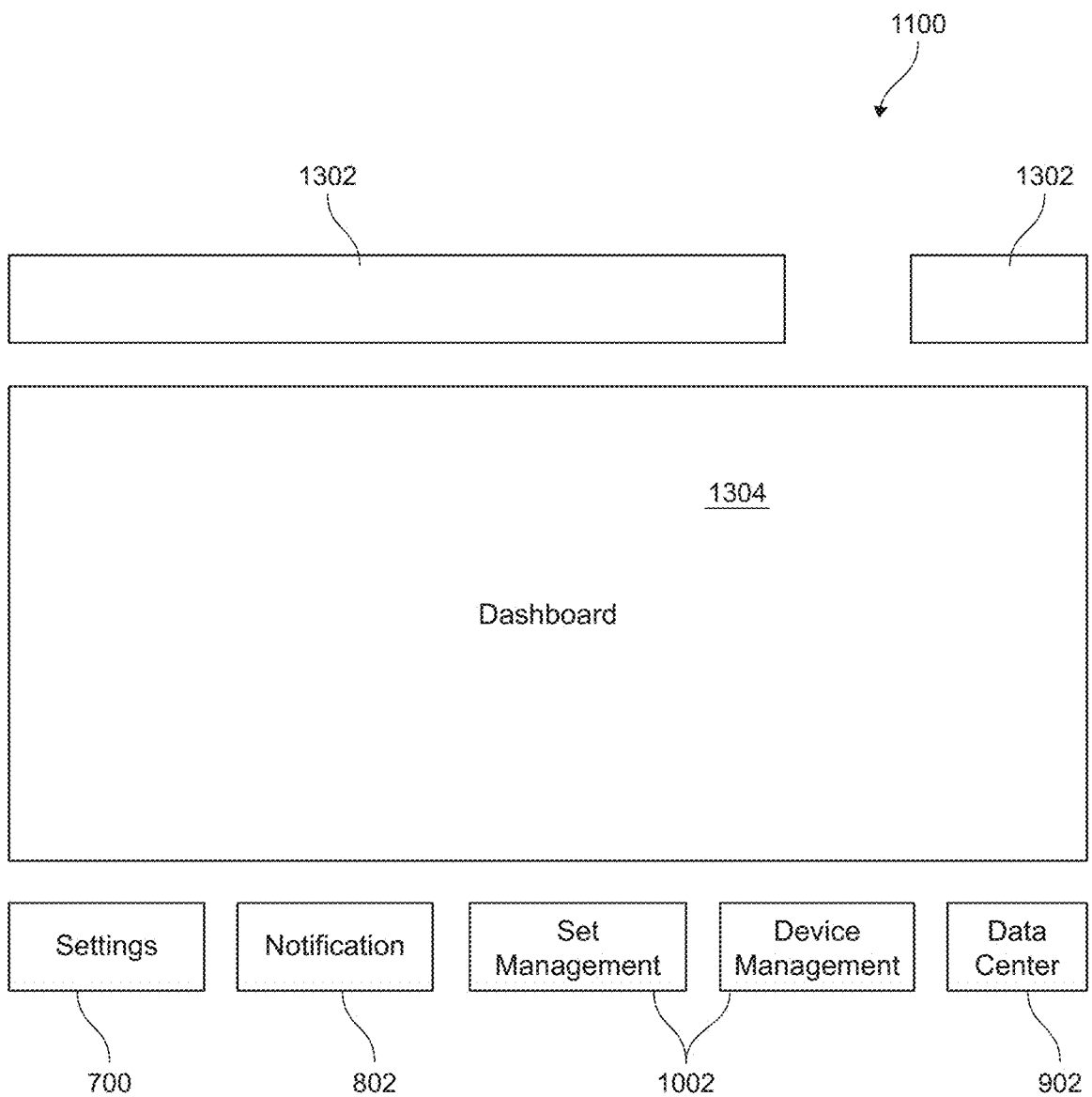
FIG. 13 illustrates a dashboard of a central platform according to some embodiments herein.

In some embodiments, as shown in FIGS. 11-13, the data analytics platform can include display hub 1100. The display hub 1100 can be displayed as a graphical user interface (GUI) on a user device. The display hub 1100 can require an onboarding process 1102 shown in FIG. 12. The onboarding process 1100, can include an account creation form 1202, a platform administration form 1204, and account creation 1206. In some embodiments the account creation form 1202 can include one or more inputs for the user. The one or more inputs can include a user's name, a username, a password, an address, network information, a hospital name, an organization name, and/or any other relevant user information. The onboarding process can include a platform administration information form 1204. The platform administration form 1204 can include one or more administration inputs. The one or more administration inputs can include, one or more administrators' names, a level of access for each user, an organization name, a hospital name, a subscription level, and/or any other relevant administration information. The data analytics platform can automatically create an account 1206 after a user completes one or more of the account creation forms 1202 and the platform administration information form 1204. The data analytics platform can automatically create a user account and an administration account. In some embodiments, the display hub 1100 can display a welcome page prior to a display of a dashboard.

In some embodiments, the display hub 1100 can display a main dashboard 1104. As shown in FIGS. 11 and 13, the main dashboard 1104 can include settings 700, notifications 802, a data center 902, and/or device management and OEM device management 1002. In some embodiments, the display hub 1100 can include one or more information display portion 1302. In some embodiments, the one or more information display portions 1302 can display information selected by the user. In other embodiments, the one or more display portions 1302 can display a time, network information, user account information, administration information, notification information and/or any other information related to the data analytics platform. In some embodiments, the display hub 100 can display a dashboard 1304. The dashboard 1304 can display information about one or more tracking devices connected to the data analytics platform. The dashboard 1304 can display a number of tracking devices, a number of drops for each tracking device or instrument, a number of sterilizations, a number of devices or instruments used per surgery, a number of devices used per surgery type, a number of trays, a number of damaged tracking devices, a location of each tracking devices or instrument, a number of active trays, and/or any other information related to the tracking devices.

Figure 14:
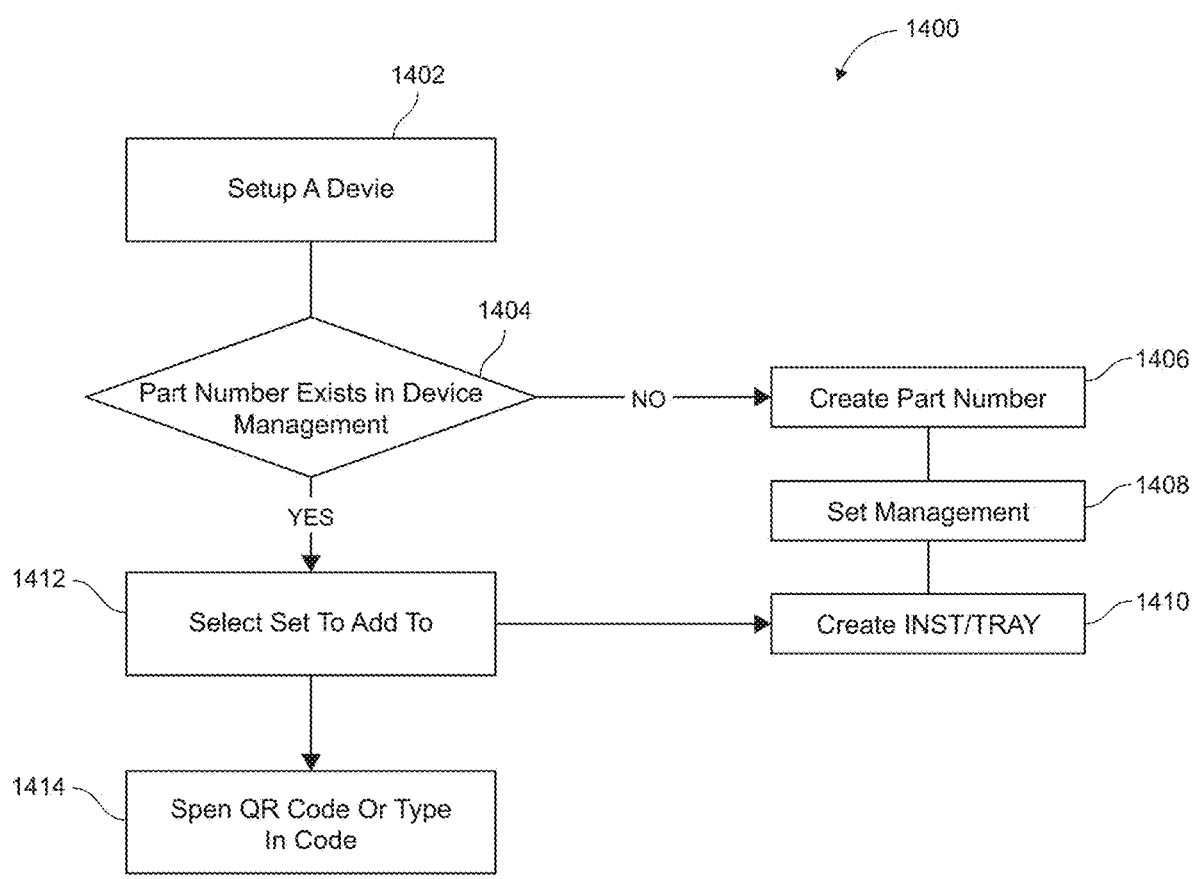
FIG. 14 illustrate a schematic of a method of setting up a tracking device according to some embodiments herein.

In some embodiments, the user can setup a device via a device setup process 1400 as shown in FIG. 14. In some embodiments, the user can select a setup a device option 1402. The setup a device option 1402 can be displayed in the display hub 1100. In some embodiments, the setup a device option 1402 can be displayed in the settings 700, the data center 902, and/or the device and OEM device management 1002. If the user selects the setup a device option 1402, the user can be directed to input a part number or device number. The system at step 1404 can determine if the part or device number in the data analytics platform by searching part or devices numbers in the device and OEM device management 1002. If the part number or device number already exists, the user can be directed to select a set to add the device to at step 1412. The set can include a group of tracking devices or smart instrument that are in a same tray, a same room, a same floor, a same department, used for a same surgery, and/or any other grouping of tracking devices or smart instruments.

If the part number or device number does not already exist, the data analytics platform can create a part number or device number and add the part number or device number to the system at step 1406. The data analytics platform, at step 1408, can direct the user to set management for the device. Set management can include selecting user devices to display information in the display hub 1100 about the part or device, setting which users the data analytics platform sends notifications to about the part or device, selecting which users can set management updates, and/or any other management or administration information about the part or device. At step 1410, the data analytics platform can create a new instrument and/or tray associated with the part or device number. After step 1410, the user can select a set to add the part or device to at step 1412.

In some embodiments, the user can add the part or device to a set by scanning or opening a QR code and/or typing in a code associated with the set or the part or device at step 1414.

Computer Systems

Figure 15:
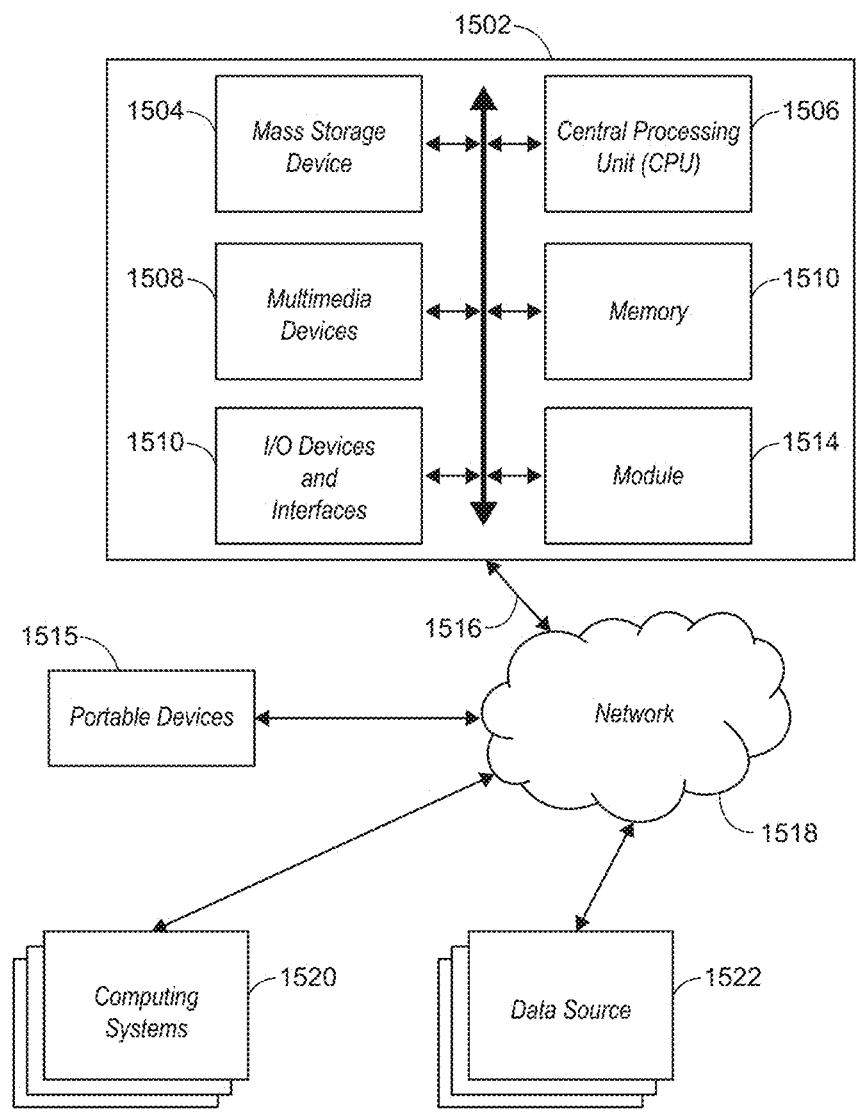
FIG. 15 illustrates a block diagram computer system according to some embodiments herein.

FIG. 15 is a block diagram depicting an embodiment of a computer hardware system configured to run software for implementing one or more embodiments disclosed herein.

In some embodiments, the systems, processes, and methods described herein are implemented using a computing system, such as the one illustrated in FIG. 15. The example computer system 1502 is in communication with one or more computing systems 1520 and/or one or more data sources 1522 via one or more networks 1518. While FIG. 15 illustrates an embodiment of a computing system 1502, it is recognized that the functionality provided for in the components and modules of computer system 1502 may be combined into fewer components and modules, or further separated into additional components and modules.

The computer system 1502 can comprise a module 1514 that carries out the functions, methods, acts, and/or processes described herein. The module 1514 is executed on the computer system 3102 by a central processing unit 1506 discussed further below.

In general, the word "module," as used herein, refers to logic embodied in hardware or firmware or to a collection of software instructions, having entry and exit points. Modules are written in a program language, such as JAVA, C or C++, Python, or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1502 includes one or more processing units (CPU) 1506, which may comprise a microprocessor. The computer system 1502 further includes a physical memory 1510, such as random-access memory (RAM) for temporary storage of information, a read only memory (ROM) for permanent storage of information, and a mass storage device 3504, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1502 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1502 includes one or more input/output (I/O) devices and interfaces 1512, such as a keyboard, mouse, touch pad, and printer. The I/O devices and interfaces 1512 can include one or more display devices, such as a monitor, that allows the visual presentation of data to a user. More particularly, a display device provides for the presentation of GUIs as application software data, and multi-media presentations, for example. The I/O devices and interfaces 1512 can also provide a communications interface to various external devices. The computer system 1502 may comprise one or more multi-media devices 1508, such as speakers, video cards, graphics accelerators, and microphones, for example.

The computer system 1502 may run on a variety of computing devices, such as a server, a Windows server, a Structure Query Language server, a Unix Server, a personal computer, a laptop computer, and so forth. In other embodiments, the computer system 1502 may run on a cluster computer system, a mainframe computer system and/or other computing system suitable for controlling and/or communicating with large databases, performing high volume transaction processing, and generating reports from large databases. The computing system 1502 is generally controlled and coordinated by an operating system software, such as Windows XP, Windows Vista, Windows 7, Windows 8, Windows 10, Windows 11, Windows Server, Unix, Linux (and its variants such as Debian, Linux Mint, Fedora, and Red Hat), SunOS, Solaris, Blackberry OS, z/OS, iOS, macOS, or other operating systems, including proprietary operating systems. Operating systems control and schedule computer processes for execution, perform memory management, provide file system, networking, and I/O services, and provide a user interface, such as a graphical user interface (GUI), among other things.

The computer system 1502 illustrated in FIG. 15 is coupled to a network 1518, such as a LAN, WAN, or the Internet via a communication link 1516 (wired, wireless, or a combination thereof). Network 1518 communicates with various computing devices and/or other electronic devices. Network 1518 is communicating with one or more computing systems 1520 and one or more data sources 1522. The module 1514 may access or may be accessed by computing systems 1520 and/or data sources 1522 through a web-enabled user access point. Connections may be a direct physical connection, a virtual connection, and other connection type. The web-enabled user access point may comprise a browser module that uses text, graphics, audio, video, and other media to present data and to allow interaction with data via the network 1518.

Access to the module 1514 of the computer system 1502 by computing systems 1520 and/or by data sources 1522 may be through a web-enabled user access point such as the computing systems' 1520 or data source's 1522 personal computer, cellular phone, smartphone, laptop, tablet computer, e-reader device, audio player, or another device capable of connecting to the network 1518. Such a device may have a browser module that is implemented as a module that uses text, graphics, audio, video, and other media to present data and to allow interaction with data via the network 1518.

The output module may be implemented as a combination of an all-points addressable display such as a cathode ray tube (CRT), a liquid crystal display (LCD), a plasma display, or other types and/or combinations of displays. The output module may be implemented to communicate with input devices 1512 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 1502 may comprise a physical or logical connection established between a remote microprocessor and a mainframe host computer for the express purpose of uploading, downloading, or viewing interactive data and databases online in real time. The remote microprocessor may be operated by an entity operating the computer system 1502, including the client server systems or the main server system, an/or may be operated by one or more of the data sources 1522 and/or one or more of the computing systems 1520. In some embodiments, terminal emulation software may be used on the microprocessor for participating in the micro-mainframe link.

In some embodiments, computing systems 1520 who are internal to an entity operating the computer system 1502 may access the module 1514 internally as an application or process run by the CPU 1506.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 1502 may include one or more internal and/or external data sources (for example, data sources 1522). In some embodiments, one or more of the data repositories and the data sources described above may be implemented using a relational database, such as Sybase, Oracle, CodeBase, DB2, PostgreSQL, and Microsoft® SQL Server as well as other types of databases such as, for example, a NoSQL database (for example, Couchbase, Cassandra, or MongoDB), a flat file database, an entity-relationship database, an object-oriented database (for example, InterSystems Caché), a cloud-based database (for example, Amazon RDS, Azure SQL, Microsoft Cosmos DB, Azure Database for MySQL, Azure Database for MariaDB, Azure Cache for Redis, Azure Managed Instance for Apache Cassandra, Google Bare Metal Solution for Oracle on Google Cloud, Google Cloud SQL, Google Cloud Spanner, Google Cloud Big Table, Google Firestore, Google Firebase Real-time Database, Google Memorystore, Google MongoDB Atlas, Amazon Aurora, Amazon DynamoDB, Amazon Redshift, Amazon ElastiCache, Amazon MemoryDB for Redis, Amazon DocumentDB, Amazon Keyspaces, Amazon Neptune, Amazon Timestream, or Amazon QLDB), a non-relational database, or a record-based database.

The computer system 1502 may also access one or more databases 1522. The databases 1522 may be stored in a database or data repository. The computer system 1502 may access the one or more databases 1522 through a network 1518 or may directly access the database or data repository through I/O devices and interfaces 1512. The data repository storing the one or more databases 1522 may reside within the computer system 1502.

Additional Embodiments

In the foregoing specification, the systems and processes have been described with reference to specific embodiments thereof. It will, however, be evident that various modifications and changes may be made thereto without departing from the broader spirit and scope of the embodiments disclosed herein. The specification and drawings are, accordingly, to be regarded in an illustrative rather than restrictive sense.

Indeed, although the systems and processes have been disclosed in the context of certain embodiments and examples, it will be understood by those skilled in the art that the various embodiments of the systems and processes extend beyond the specifically disclosed embodiments to other alternative embodiments and/or uses of the systems and processes and obvious modifications and equivalents thereof. In addition, while several variations of the embodiments of the systems and processes have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosed systems and processes. Any methods disclosed herein need not be performed in the order recited. Thus, it is intended that the scope of the systems and processes herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and sub-combinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

It will also be appreciated that conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the embodiments are not to be limited to the particular forms or methods disclosed, but, to the contrary, the embodiments are to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (for example, as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (for example, as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein but are to be accorded the widest scope consistent with this disclosure, the principles and the novel features disclosed herein.

What is claimed is:

1. A device for tracking a surgical instrument comprising:
 a sensor configured to detect a location event associated with the surgical instrument;
 a circuit for controlling and processing signals coming from the sensor;
 a communication module for wirelessly transmitting information to an external device;
 a memory for storing information coming from the circuit; and
 a power source configured to supply power to sensor, the communication module, the circuit, and the memory,
 wherein the device is configured to be coupled to a tray configured to hold the surgical instrument, and wherein the device is configured to:
  determine a location event reaching a threshold level;
  determine a location of the device when sensor detects a location event;
  compare the location to a previous location stored on the memory;
  determine that the location is different from the previous location; and
  in response to determining that the location is different from the previous location, wirelessly transmit, by the communication module, the location to an external system.

2. The device of claim 1, wherein the sensor comprises at least one of: a mechanical switch, a magnetic field sensor, an accelerometer, a temperature sensor, a photosensor, a pressure sensor, a proximity sensor, or a vibrometer.

3. The device of claim 1, wherein the location event comprises an acceleration, a change in temperature, a change in light, a change in pressure, a change in magnetic field, or a vibration.

4. The device of claim 1, wherein the device is further configured to periodically activating the sensor to monitor the location of the device at predetermined times.

5. The device of claim 1, wherein the device is further configured to automatically determine the location of the device in response to not detecting any location event for a period of time.

6. The device of claim 1, wherein the device is further configured to: transmit data to a data analytics platform via at least one of: a cellular network, Wi-Fi, Bluetooth, or RFID.

7. The device of claim 1, wherein the communication module comprises a radio interface.

8. The device of claim 1, wherein the sensor comprises a temperature sensor, wherein the device is further configured to:
  determine that a temperature has increased above a threshold temperature; and
  disable power to at least one component of the device comprising at least one of: a radio interface, the memory, or a counter.

9. The device of claim 8, wherein the device is further configured to:
  determine that a temperature has decreased above the threshold temperature; and
  enable power to the at least one component.

10. The device of claim 1, wherein the location event occurs when the device is removed from an autoclave, and wherein the device is configured to:
  increment, by the circuit, a counter stored in the memory; and
  transmit, by the communication module, the counter to a data analytics platform.

11. A method for tracking a surgical instrument comprising using a tracking device:
  configuring a sensor of the tracking device to detect a location event associated with the surgical instrument;
  determining, by the tracking device using a sensor, a location event;
  determining, by the tracking device, that the location event meets a threshold level;
  determining, by the tracking device, a location of the tracking device when the sensor detects the location event;
  comparing, by the tracking device, the location to a previous location stored in a memory of the tracking device;
  determining, by the tracking device, that the location is different from the previous location; and
  in response to determining that the location is different from the previous location, wirelessly transmitting, by a communication module of the tracking device, the location to an external system.

12. The method of claim 11, where the location event comprises one or more of: an acceleration, a change in temperature, a change in light, a change in pressure, a change in magnetic field, or a vibration.

13. The method of claim 11, further comprising:
  periodically monitoring the location of the tracking device at a predetermined time interval.

14. The method of claim 11, further comprising: configuring the communication module to automatically determine the location of the tracking device coupled to a tray if the sensor does not detect the location event for a period of time.

15. The method of claim 11, further comprising: transmitting data to a data analytics platform via at least one of: a cellular network, Wi-Fi, Bluetooth, or RFID.

16. The method of claim 11, further comprising:
  determining that a temperature has increased above a threshold temperature; and
  disabling power to at least one component of the tracking device, the at least one component comprising at least one of: a radio interface, a memory, or a counter.

17. The method of claim 16, further comprising:
  determining that the temperature has decreased above the threshold temperature; and
  enabling power to the at least one component.

18. The method of claim 11, further comprising:
  incrementing, by the tracking device, a counter stored in a memory of the tracking device; and
  transmitting, by the communication module, the counter to a data analytics platform.

19. The method of claim 11, wherein the communication module comprises a radio interface.

20. The method of claim 11, wherein the sensor comprises at least one of: a mechanical switch, a magnetic field sensor, an accelerometer, a temperature sensor, a photosensor, a pressure sensor, a proximity sensor, or a vibrometer.

* * * * *